United States Patent [19]
Gall et al.

[11] Patent Number: 4,481,360
[45] Date of Patent: Nov. 6, 1984

[54] 4H-1,2,4-TRIAZOL-3-YL COMPOUNDS

[75] Inventors: Martin Gall; John R. Palmer, both of Kalamazoo, Mich.

[73] Assignee: The Upjohn Company, Kalamazoo, Mich.

[21] Appl. No.: 527,156

[22] Filed: Aug. 26, 1983

[51] Int. Cl.³ .................................................. C07D 401/04
[52] U.S. Cl. ....................................... 546/210; 424/267
[58] Field of Search ............................................ 546/210

[56] References Cited

U.S. PATENT DOCUMENTS 3,962,237 6/1976 Boyle et al. ........................ 546/210
4,318,913 3/1982 Clitherow et al. ................. 546/210
4,338,453 7/1982 Gall ..................................... 546/210

OTHER PUBLICATIONS

Bohm, et al., Die Pharmazie 36:246, (1981).
Behringer, et al., Liebigs Ann. Chem. 1264, (1975).
Derwent Farmdoc No. 17865E, (corresponding to Belgian Pat. 890,035).

Primary Examiner—Robert T. Bond
Attorney, Agent, or Firm—Lawrence T. Welch

[57] ABSTRACT

The present invention provides novel 4-phenyl-triazol-3-yl- and 3-phenyl-triazol-4-yl-piperidines which are useful as analgesics.

7 Claims, No Drawings

4H-1,2,4-TRIAZOL-3-YL COMPOUNDS

DESCRIPTION

Background

The present invention provides novel compositions of matter. More particularly, the present invention provides novel 4-phenyl-triazol-3-yl- and 3-phenyl-triazol-4-yl- piperidines which are useful as analgesics. Some of these compounds are also useful as anti-psychotic agents.

Relief of pain is of course one of the primary objectives in medicine. Drugs which have a predominant pain relieving action are called analgesics and commonly classified as narcotic and non-narcotic. This classification scheme is based on legal considerations, since there is greater federal regulation of narcotic analgesics over non-narcotic analgesics. A more useful classification scheme is to classify the analgesics as strong, moderate and mild analgesics. Most narcotic analgesics are strong analgesics and most non-narcotic analgesics are mild to moderate analgesics.

The narcotic analgesics include the alkaloids of opium and numerous related synthetic drugs. These include, for example, naturally occuring alkaloids and semi-synthetic opiates, meperidine and related phenyl-piperidines, methadone and related drugs, benzomorphans, morphinan derivatives, and narcotic antagonists. The non-narcotic, or mild to moderate analgesics include the salicylates, pyrazolones, para-aminophenol derivatives, and a class of non-steroidal anti-inflammatory compounds including indomethacin, mefenamic acid, ibuprofen, fenoprofen, naproxen, and tolmetin.

What is needed in the art is an analgesic which relieves pain similar to narcotic analgesics without the side effects associated with these analgesics.

PRIOR ART

Böhm, et al., Die Pharmazie 36:246 (1981) discloses certain phenyl substituted 1,3,4-triazoles which are stated to be useful as analgetics and/or anti-phlogistics. Behringer, et al., Liebigs Ann. Chem. 1264 (1975) describes the metallation of a triazole ring with butyllithium and condensation of the anion thus formed with ketones. Derwent Farmdoc No. 17865E, corresponding to Belgian Pat. No. 890,035 (Roussel UCLAF) discloses certain phenyl substituted 1,3,4-triazoles which are stated to be useful as analgesics to treat nerve, muscle or joint pain or toothache.

SUMMARY OF THE INVENTION

The present invention particularly provides:
a compound of the Formula I wherein either
(1) $R_{10}$ is a substituent of the Formula II and $R_{20}$ is a substituent of the Formula III or
(2) $R_{10}$ is a substituent of the Formula IV and $R_{20}$ is a substituent of the Formula II;
wherein the wavy lines represent the cis or trans configuration;
  wherein $R_{31}$ is
   (a) hydrogen,
   (b) $C_1$ to $C_2$-alkyl,
   (c) —SCH$_3$,
   (d) —S(O)CH$_3$,
   (e) —S—phenyl,
   (f) —S(O)—phenyl,
   (g) —CH(OH)CH$_3$,
   (h) —CH$_2$OC(O)R$_{11}$, or
   (i) phenyl,
with the provisos that
   (1) when $R_{20}$ is the Formula III substituent, $R_{31}$ is —SCH$_3$, —S(O)CH$_3$, —S—phenyl, —S(O)—phenyl, —CH(OH)CH$_3$ or —CH$_2$OC(O)R$_{11}$ only when $R_3$ is hydrogen and
   (2) $R_{31}$ is phenyl only when $R_{20}$ is the Formula III substituent and $R_3$ is —OC(O)R$_{21}$;
  wherein $X_1$ is
   (a) o-, m-, or p-fluoro;
   (b) hydrogen,
   (c) methoxy,
   (d) m-acetoxy, or
   (e) ($C_1$-$C_2$)alkyl;
  wherein $Y_1$ is
   (a) hydrogen,
   (b) m-methoxy, or
   (c) ($C_1$-$C_2$)alkyl;
with the provisos that $Y_1$ is m-methoxy only when $X_1$ is p-methoxy; and $Y_1$ is ($C_1$-$C_2$)alkyl only when $X_1$ is ($C_1$-$C_2$)alkyl;
  wherein $R_1$ is
   (a) hydrogen,
   (b) —CH$_3$,
   (c) —C$_2$H$_5$, or
   (d) CH$_2$=CH—CH$_2$—,
with the proviso that $R_1$ is CH$_2$=CH—CH$_2$— only when $R_{20}$ is a Formula III substituent;
  wherein $R_2$ is
   (a) hydrogen, or
   (b) methyl;
  wherein $R_3$ is
   (a) hydrogen, or
   (b) —OC(O)R$_{21}$;
  wherein $R_{11}$ and $R_{21}$ are the same or different and are hydrogen, methyl and ethyl; and the pharmacologically acceptable salts thereof.

Thus, the compounds of the present invention are of the Formulas Ia and Ib.

Compounds of the present invention have been evaluated in at least one of the following standard laboratory tests which demonstrate analgesic activity. Thus, the compounds of the present invention have been evaluated in the in vivo tests conducted on mice known as the "tail flick"; the "tail pinch"; and the "HCl writhing" tests which may be briefly described as follows:

Procedure—Groups of 6 Carworth Farms (CF-1)-derived mice, weighing 18 to 22 grams, are used. A solution or suspension of the test compound is administered subcutaneously at a dose of 100 mg/kg. Fifteen minutes following the dosing, a series of procedures are carried out as follows:

Tail Flick: A high intensity light is directed at the middle third of the test animal's tail, simultaneous with the start of a photoelectric timer. The number of seconds required for the animal to "flick" its tail out of the light path is recorded.

Tail Pinch: A bulldog arterial clamp is applied to the base of a test animal's tail, and the number of animals that do not turn within 30 seconds are recorded.

HCl Writhing: The test animals receive an intraperitoneal dose of 0.15 percent hydrochloric acid solution, one ml, per 100 g body weight. The number of animals failing to writhe within 15 minutes is recorded.

Evaluation: Analgesia is measured by the Tail Flick, Tail Pinch, and Writhing responses. In the latter two cases, where the animals fail to respond within the measuring time interval the compound is scored as analgesic. Where the tail flick time is more than 2 standard derivations greater than mean for the control group, the compound is scored as analgesic.

Test compounds scored as analgesic in at least 5 of 6 animals are retested at multiple dose levels for estimation of $ED_{50}$ values calculated by the methods of Spearman and Karber (in D. J. Finney, "Statistical Methods in Biological Assay," Hafner Publ. (1952)).

These comounds have also been evaluated in an in vitro opiate receptor binding assay, which demonstrates narcotic analgesic-like activity. For a discussion of opiate receptor binding assays, see, e.g., Pert, et al., Proc. Nat. Acad. Sci. USA, 70:2243 (1973).

All of the compounds of the present invention have been found active in one or more of these tests. Some of the compounds of this invention are more preferred as they are active in the in vivo mouse analgesia tests, but show little or no activity in the opiate receptor binding assay, meaning that the compound is an effective analgesic agent, without the detrimental side effects of narcotic analgesics. A compound of this type is 1-(2-phenylethyl)-4-(4-phenyl-4H-1,2,4-triazol-3-yl)-piperidine (Example 12). $(3\alpha,4\beta)$-3-Methyl-4-(5-methyl-4-phenyl-4H-1,2,4-triazol-3-yl)-1-(2-phenylethyl)-4-piperidinol, acetate (ester) and its monohydrochloride isomer B (Example 4, Part C) are preferred for subcutaneous administration, having an $ED_{50}$ in the Tail Flick, Tail Pinch and HCl Writing tests of approximately 0.004 mg/kg.

By virtue of their analgesic activity the compounds of Formula I are useful in treating pain in humans and animals. A physician or veterinarian of ordinary skill readily determines a subject who is in need of analgetic treatment. Regardless of the route of administration selected, the compounds of the present invention are formulated into pharmaceutically acceptable dosage forms by conventional methods known to the pharmaceutical art.

The compounds can be administered in such oral unit dosage forms as tablets, capsules, pills, powders, or granules. They also may be administered rectally or vaginally in such forms as suppositories or bougies. They may also be introduced parenterally, (e.g., subcutaneously, intravenously, or intramuscularly), using forms known to the pharmaceutical art. In general, the preferred route of administration is oral.

An effective but non-toxic quantity of the compound is employed in treatment. The dosage regimen for treating pain by the compounds of this invention is selected in accordance with a variety of factors including the type, age, weight, sex, and medical condition of the mammal, the severity of the pain, the route of administration and the particular compound employed. An ordinarily skilled physician or veterinarian will readily determine and prescribe the effective amount of the compound of the present invention to prevent, arrest, lessen or eliminate the sensation of pain. In so proceeding, the physician or veterinarian could employ relatively low dosages at first, subsequently increasing the dose until a maximum response is obtained.

Initial dosages of the compounds of the invention are ordinarily in the area of 0.01 mg/kg up to at least 10 mg/kg per dose orally, preferably 0.1 to 5 mg/kg orally and are given from one to four times daily or as needed. When other forms of administration are employed equivalent doses are administered. When dosages beyond 10 mg/kg are employed, care should be taken with each subsequent dose to monitor possible toxic effects.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate, cyclohexanesulfamate, methanesulfonate, ethanesulfonate, benzenesulfonate, toluenesulfonate and the like. Such acid addition salts are prepared by known methods. Additionally, the compounds of this invention may be administered in a suitable hydrated form.

The compounds of the present invention are prepared by the methods depicted in Charts A, B and C. In these charts $R_5$ is phenyl, $R_6$ is hydrogen or methyl, $R_{30}$ is hydrogen, methyl, ethyl, or phenyl, $R_{32}$ is methyl, ethyl, methylthio, phenylthio, —CH(OH)CH$_3$, or —CH$_2$OC(O)R$_{11}$, and $X_1$, $Y_1$, $R_1$, $R_2$, $R_3$, $R_{11}$, and $R_{21}$ are as defined above (unless otherwise noted). Compounds produced as in these charts can be isolated and purified by known methods, for example, extraction, crystallization, column chromatography, and the like. The required starting materials for the procedures of these charts are known or can be prepared by known methods. As used herein ambient temperature refers to the prevailing room temperature usually about 20° to 23° C.

The procedures of Chart A are used to prepare compounds of the Formula Ia wherein $R_3$ is —OC(O)R$_{21}$. In Chart A, a heterocycle of the Formula A-1 (prepared by methods similar to those described in U.S. Pat No. 4,338,453) containing a reactive C—H or C—Br bond is dissolved in tetrahydrofuran (THF), cooled to −78° to −30° C., is treated with a solution of n- or sec-butyllithium in hexane or pentane, and stirred one tenth to one half hour until anion formation is substantially complete.

The bromo compound of the Formula A-1 can be prepared from the anion of a Formula A-1 compound by reaction with bromine at low temperature (down to approximately −78° C.) followed by allowing the mixture to warm to room temperature and conventional isolation procedures.

The heterocyclic anion thus formed from a Formula A-1 compound is treated with a solution of the phenethylpiperidone of the Formula A-2 in THF at −30° C. and warmed slowly to ambient temperature, to produce an amino alcohol of the Formula A-3.

Following the procedures of H. Vorbrüggen (Angew Chem Int Ed. Eng. 17, 569 (1978)) a solution of 5.15 mmol of amino alcohol (Formula A-3) dissolved in 40 ml methylene chloride is treated with 2-10 equivalents of triethylamine, 2-5 equivalents of acid anhydride (or formic acid) and 0.2-0.8 equivalents of 4-(dimethylamino)pyridine at a temperature of from −40° C. to room temperature to yield the Formula A-4 product.

Alternatively esterification is achieved by reaction of a Formula A-3 alcohol with an appropriate mixed anhydride, for example that of acetic and formic acids, in the presence of pyridine at 0° C. to ambient temperature for a time sufficient to form the desired ester (usually up to about 18 hours).

When a Formula A-4 compound wherein $X_1$ is m-acetoxy is desired, it is prepared from a Formula A-3 compound wherein $X_1$ is m-methoxy, which is treated with 48% aqueous hydrogen bromide at reflux for a time sufficient to form the corresponding intermediate compound wherein $X_1$ is hydroxy (usually about 18 hours). Esterification with acetic anhydride as described above then forms a diester of the Formula A-4 wherein $X_1$ is m—OC(O)CH$_3$ and $R_{21}$ is methyl. Selective hydrolysis of the phenol ester with potassium bicarbonate in aqueous methanol then produces a compound of the Formula A-4 wherein $X_1$ is hydroxy and $R_{21}$ is methyl, which compound is used as an intermediate for preparing other desired A-4 esters wherein $X_1$ is m-acetoxy.

As an alternative to the conversion of A-1 to A-3 by reaction with A-2 as in Chart A, a piperidone similar to A-2 but bearing on the piperidone nitrogen a benzyl rather than a 2-phenylethyl group is reacted with the anion from the A-1 compound. Hydrogenolysis of the benzyl group then yields an alcohol similar to A-3 but bearing a hydrogen on the piperidine nitrogen. Reaction of this compound with 2-phenylethyl bromide then produces the 2-phenylethyl compound of the Formula A-3.

The procedures of Chart B are used to prepare compounds of the Formula Ia wherein $R_3$ is hydrogen. In Chart B, the isonicotinic acid hydrazide (Formula B-1) is treated with an appropriately substituted phenyl isothiocyanate (Formula B-2) in ethanol to give the Formula B-3 compound by a known method (see for example U.S. Pat. No. 4,338,453).

This product is treated with an aqueous 10–40% solution of sodium hydroxide and refluxed for 1–3 hours to produce the crude product of Formula B-4 which is filtered and cautiously added in small portions to a hot solution of 20% nitric acid heated on a steam bath to produce the Formula B-5 compound. A vigorous frothing occurs on adding each portion of sulfide.

The phenyl triazolo pyridine (Formula B-5) dissolved in acetic acid is treated with an amount preferably an equal weight of a platinum oxide catalyst and hydrogenated in a Parr Bomb at 50 psi initial pressure. The catalyst is filtered, the acetic acid is removed in vacuo and the product of the Formula B-6 is neutralized and crystallized from a suitable solvent if desired.

The secondary piperidine (Formula B-6) is treated with 1.6 equivalents of phenethyl bromide, 1.4 equivalents of potassium carbonate in absolute ethanol (approximately 0.3M) and refluxed for 24 hr. After workup from aqueous sodium hydroxide and chloroform extraction, the Formula B-7 product is crystallized.

The anion of the compound of the Formula B-7 is generated at $-78°$ to $-30°$ C. in THF as in Chart A and is treated with:
(a) methyl or ethyl iodide,
(b) dimethyl disulfide,
(c) diphenyl disulfide,
(d) acetaldehyde, or
(e) formaldehyde followed by suitable esterification to produce a compound of the Formula B-8 wherein $R_{32}$ is, respectively,
(a) methyl or ethyl,
(b) methylthio,
(c) phenylthio,
(d) —CH(OH)CH$_3$, or
(e) —CH$_2$OC(O)R$_{11}$.

When this reaction is undertaken using methyl iodide, both 5-methyl and 5-ethyl-triazole products result. The methylthio and phenylthio compounds of the Formula B-8 are oxidized to the corresponding sulfoxide with a suitable oxidant under acidic conditions so as to avoid oxidation of nitrogen, for example with hydrogen peroxide in acetic acid.

As an alternative a Formula B-7 compound is reacted directly with paraformaldehyde in a suitable hydrocarbon solvent such as xylene at elevated temperature for a time sufficient to form the hydroxymethyl compound (see U.S. Pat. No. 4,338,453) which is esterified to produce a compound of the Formula B-8 wherein $R_{32}$ is —CH$_2$OC(O)R$_{11}$.

The procedures of Chart C are used to prepare compounds of the Formula Ib of this invention. In Chart C following the procedure of Lobbezoo, Journal of Medicinal Chemistry, Vol. 24, 777 (1981), a piperidone of the Formula C-1 ($R_1$ is not CH$_2$=CH—CH$_2$—) is reacted with hydrogen gas and benzylamine in the presence of some thiophene and 10% palladium on carbon (Pd/C) in methanol to produce the compound of the Formula C-2, which upon further hydrogenolysis over fresh Pd/C is converted to the amine of the Formula C-3. Alternatively the Formula C-3 amine is produced by reaction of the Formula C-1 piperidone with hydroxylamine to produce the Formula C-4 oxime which is reduced with sodium in ethanol to produce the Formula C-3 amine. This C-1 to C-4 to C-3 route must be used if $R_1$ is CH$_2$=CH—CH$_2$—. In the C-1 to C-4 to C-7 route the sequence can be carried out with a benzyl rather than 2-phenylethyl group on the piperidone nitrogen. After triazole ring formation the benzyl group is removed by hydrogenolysis and the resulting piperidine nitrogen is alkylated with 2-phenylethyl bromide as described above. Reaction of the Formula C-3 amine with N,N-dimethylformamide dimethyl acetal at reflux for about 3 hours produces the amidine of the Formula C-5 which is heated with the appropriate benzoic acid hydrazide first at 55° C. for about 14 hours to produce the Formula C-6 compound and then at reflux for about 4 hours to produce the compound of the Formula C-7. As described above for the Formula B-7 compound, the formula C-7 triazole is converted to its anion and reacted to produce the various Formula C-8 compounds. The Formula C-8 sulfoxides are prepared as described above.

Note that for compounds of the Formula I and more particularly for compounds of the Formulas Ia and Ib, up to three carbon atoms of the piperidine ring may be asymmetrically substituted and thus may independently possess the R or S configuration. The Formula I compounds may thus have as many as 8 stereoisomers which comprise four pairs of enantiomers; each enantiomeric pair is termed a racemate. See for example J. B. Hendrickson, et al., Organic Chemistry, Third Edition, McGraw-Hill Book Company, New York, N.Y. 1970, pages 198–230, particularly pages 207, 208, 213, and 215 thereof. The four possible racemates of the Formula I compounds can each exist as a mixture of the two enantiomers or each enantiomer of each pair can be separated and obtained substantially free of other enantiomers. Varying mixtures of enantiomers are also possible. All such stereoisomers resulting from asymmetric substitution at up to three carbon atoms of the piperidine ring of Formula I compunds are within the scope of this invention.

When it is desired to specify for a Formula I compound or intermediate therefor the configuration of the other asymmetric centers relative to that of the lowest numbered asymmetric carbon atom, this is done according to the Chemical Abstracts Service publication, "Naming and Indexing of Chemical Substances for CHEMICAL ABSTRACTS during the Ninth Collective Period (1972–76)," a reprint of Section IV (Selection of Index Names for Chemical Substances) from the CHEMICAL ABSTRACTS Volume 76 Index Guide. Accordingly, the relative stereochemistry of three asymmetric carbon atoms in the piperidine ring of Formula I compounds is indicated by:

(1) the arbitrary designation of $3\alpha$ for the orientation of the substituent on the lowest numbered (asymmetric) carbon atom (here explicitly chosen as carbon atom number 3);

(2) the designation $4\alpha$ or $4\beta$ when the substituent on (asymmetric) carbon atom number four is on the same or opposite side of the plane of the piperidine ring, respectively, relative to said $C_3$-substituent; and (3) the designation $5\alpha$ or $5\beta$ when the substituent on (asymmetric) piperidine ring carbon atom number 5 is on the same or opposite side of the plane of the piperidine ring, respectively, relative to said $C_3$-substituent.

When carbon atom number 4 of the piperidine ring (the $R_3$-bearing carbon atom in the Formula Ia compounds) bears two non-hydrogen groups, the $\alpha$ or $\beta$ is applied to the group with the higher preference according to the sequence rule. This higher preference is determined by a number of criteria, the first of which is greater preference for higher atomic number of the atom attached to carbon atom number 4. For references on the sequence rule see:

(a) Journal of Organic Chemistry, Vol. 35, pages 2849–2867, (1970); and (b) R. S. Cahn, Journal of Chemical Education, Vol. 41, pages 116–125, (1964). For example, for a compound of the Formula Ia wherein $R_1$ is methyl, $R_2$ is hydrogen, and $R_3$ is —OC(O)CH$_3$ which is cis to the $R_1$ methyl group, the descriptor $(3\alpha,4\alpha)$ is applied to the name. This results because, of the two substituent atoms bonded to $C_4$ of the piperidine ring, namely:

(1) the oxygen atom of —OC(O)CH$_3$ and (2) the carbon atom ($C_3$) of the triazole ring, the oxygen has the greater atomic number and therefore the higher preference. The description for the methyl group on $C_3$ of the piperidine ring is arbitrarily $3\alpha$, and since the —OC(O)CH$_3$ group (on $C_4$ of the piperidine ring) is cis to the methyl group on $C_3$, the correct description of the relative stereochemistry of the two groups is $(3\alpha,4\alpha)$. An example is the compound of Example 3, Part D below.

When it is desired to specify the absolute configuration of an asymmetrically substituted carbon atom of a Formula I compound this is done using the appropriate R- or S-designation as is customary.

Two isomers which differ only in the stereochemistry at one asymmetric carbon atom of the piperidine ring may be referred to as epimers.

If desired the Formula I compounds of this invention can be resolved into their substantially separated (+)- or (−)-enantiomers by methods known in the art. In this case, the optical resolution can be done by at least two different routes. The resolving agents by either route are any of the known resolving agents such as optically active camphorsulfonic acid, bis-o-toluoyltartaric acid, tartaric acid, and diacetyl tartaric acid and the like which are commercially available and which are commonly used for resolution of amines (bases), as for example in Organic Synthesis, Coll. Vol. V, p. 932 (1973), resolution of R-(+) and S-(−)-α-phenylethylamine with (−)-tartaric acid.

By the first method for reesolving the compounds of this invention, for example, one of the Formula I compounds or Formula A-3 compounds of Chart A can be converted into its optically active diastereomeric salts by reaction with an optically active compound, for example and acid—examples mentioned above—in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous base the corresponding optically active enantiomers of the compound can be obtained, each of which can subsequently and separately be converted to the desired acid addition salt or to a desired ester of this invention and then to an acid addition salt.

By the second method the precursor compounds of the Formulas A-2 of Chart A can first be resolved into substantially separated (+)- and (−)-enantiomers and then the separated enantiomers can be separately reacted as for Formula A-2 compounds in Chart A. Subsequent purification is then carried out for the Formula A-3 or A-4 compounds.

For compounds of this invention containing a sulfoxide (—S(O)—) moiety, compounds stereoisomeric at sulfur are possible and such stereoisomers and mixtures thereof are within the scope of this invention.

Certain compounds of the present invention are preferred. Thus compounds of the Formula I expressed by the Formula Ia and Ib wherein $R_2$ is hydrogen, and $R_{31}$, $X_1$, $Y_1$, $R_1$, and $R_3$ are as defined above are preferred. More preferred are compounds of the preferred group wherein $R_{31}$ is hydrogen or methyl, $X_1$ is hydrogen, $C_1$ to $C_2$-alkyl in the ortho position, or methoxy, $Y_1$ is hydrogen, m-methoxy, or $C_1$ to $C_2$-alkyl, and $R_1$ is hydrogen or methyl in either stereochemical orientation. Most preferred are the compounds of this latter group wherein $Y_1$ is hydrogen or $C_1$ to $C_2$-alkyl in the ortho position.

DESCRIPTION OF THE PREFERRED EMBODIMENTS

The present invention is seen more fully by the examples given below. Temperatures given are in degrees Centigrade (°C.).

EXAMPLE 1

4-[4-(3-methoxyphenyl)-5-methyl-4H-1,2,4-triazol-3-yl]-1-(2-phenylethyl)-4-piperidinol, acetate (ester) (Formula Ia: $X_1$ is m—OCH$_3$, $Y_1$ is H, $R_3$ is OC(O)CH$_3$, $R_{31}$ is —CH$_3$, and $R_1$ and $R_2$ are hydrogen).

PART A

4-[4-(3-Methoxyphenyl)-5-methyl-4H-1,2,4-triazol-3-yl]-1-(2-phenylethyl)-4-piperidinol (Formula Ia: $X_1$ is m—OCH$_3$, $Y_1$ is H, $R_3$ is OH, $R_{31}$ is —CH$_3$, and $R_1$ and $R_2$ are hydrogen).

Refer to Chart A (conversion of A-1 to A-3).

To a stirred mixture of 3.8 g (0.02 mole) of 4-(3-methoxyphenyl)-3-methyl-4H-1,2,4-triazole in 150 ml of tetrahydrofuran at −78° C. (dry ice-isopropanol both) under an atmosphere of nitrogen is added dropwise 13.0 ml (0.02 mole) of 1.6N n-butyllithium in hexane (Aldrich Chemical Co.). The new mixture is stirred between −78° and −40° C. for 10 min before recooling to −78° C. A solution of 4.1 g (0.02 mole) of 1-(β-phenethyl)-4-piperidone (Aldrich Chemical Co.) in 50 ml of tetrahydrofuran then is added within two min. The coolant is removed and the reaction flask allowed to warm to ambient temperature over 1 hr. The reaction is quenched with 50 ml of water and the solvents are removed in vacuo. The resultant mixture is partitioned between chloroform and 10% aqueous NaOH and the phases are separated. The chloroform layer is washed with 10% aqueous sodium hydroxide, water, and brine, and then dried over sodium sulfate and concentrated in vacuo at 40° C. to yield 9.7 g of dark oil.

Crystallization of 9.7 g of this oil from an ethyl acetate-hexane mixture affords a first crop of 4.7 g (60%) of the subtitled product, with a melting point of 169°–170° C.; IR (Nujol) peak at 3200 cm$^{-1}$; NMR (CDCl$_3$ δ) peaks at 1.55–2.11, 2.16, 2.25–2.90, 3.84 and 6.75–7.5. The mass spectrum reveals peaks at m/e 392 and 374.

Anal. Calcd. for $C_{23}H_{28}N_4O_2$; MW 392.51; C, 70.38; H, 7.19; N, Found: C, 70.29; H, 7.39; N, 14.31.

PART B

4-[4-(3-methoxyphenyl)-5-methyl-4H-1,2,4-triazol-3-yl]-1-(2-phenylethyl)-4-piperidinol, acetate (ester) (Formula Ia: $R_{31}$ is methyl, $Y_1$ is H, $X_1$ is m—OCH$_3$, $R_3$ is —OC(O)CH$_3$, and $R_1$ and $R_2$ are hydrogen).

Refer to Chart A (conversion of A-3 to A-4).

To a solution of approximately 1.0 g (2.5 mmole) of starting piperidinol (the compound of Part A above), 1 ml of triethylamine and approximately 80 mg of 4-(dimethylamino)pyridine in 10 ml of methylene chloride is added 2 ml of acetic anhydride. The solution is stirred for 24 hr at ambient temperature under a nitrogen atmosphere. Aqueous 5% sodium hydroxide is added to the reaction and the phases are separated. The organic phase is washed with water, and brine, and dried over sodium sulfate and concentrated in vacuo to yield 1.4 g of a yellow-orange oil.

The oil is crystallized from ethyl acetate-hexane to afford 0.68 g (63%) of powdered titled crystals with a melting point of 144°–145°: IR (Nujol) shows a peak at 1730 cm$^{-1}$. NMR (CDCl$_3$ δ) reveals peaks at 1.76, 2.13, 2.25–2.5 2.5–219, 3.84, and 6.6–7.5. The mass spectrum reveals an ion at m/e 435.

Anal. Calcd. for $C_{25}H_{30}N_4O_3$, MW 434.55; C, 69.10; H, 6.96; N, 12.89. Found: C, 69.07; H, 7.08; N, 12.91.

EXAMPLE 2

4-[4-[3-(acetyloxy)phenyl]-5-methyl-4H-1,2,4-triazol-3-yl]-1-(2-phenylethyl)-4-piperidinol, acetate (ester), dihydrochloride (Formula Ia: $X_1$ is m—OC(O)CH$_3$, $Y_1$ is H, $R_3$ is OC(O)CH$_3$, $R_{31}$ is —CH$_3$, and $R_1$ and $R_2$ are hydrogen).

PART A

4-[4-(3-hydroxyphenyl)-5-methyl-4H-1,2,4-triazol-3-yl]-1-(2-phenylethyl)-4-Piperidinol, (Formula Ia: $X_1$ is m—OH, $Y_1$ is H, $R_3$ is OH, $R_{31}$ is —CH$_3$, and $R_1$ and $R_2$ are hydrogen).

A mixture of 0.5 g (1.27 mmol) of the methyl ether of Example 1, Part A above and 15 ml of 48% aqueous hydrobromic acid is refluxed for 18 hrs. The excess hydrobromic acid is removed in vacuo at 80° C. to yield an oily salt which then is dissolved in 10 ml of water and approximately 5 ml of 50% aqueous sodium hydroxide. The mixture is heated on a steam bath for 30 min. The solution is chilled in an ice bath and acidified with concentrated hydrochloric acid to a pH of 2. The precipitated hydrochloric acid salt is basified with a saturated solution of aqueous sodium bicarbonate to a pH of 8. The precipitate is filtered, washed several times with water and dried in vacuo at 80° C. to afford 0.4 g (83%) of the subtitled product having an $R_f$ of 0.2 (20% methanol-chloroform) with a melting point of 240°–245° C. (decomposes). The NMR spectrum is in aggreement with the desired product.

PART B

4-[4-(3-acetoxyphenyl)-5-methyl-4H-1,2,4-triazol-3-yl]-1-(2-phenylethyl)-4-piperdinol, acetate (ester), dihydrochloride (Formula Ia: $X_1$ is m—OC(O)CH$_3$, $Y_1$ is H, $R_3$ is OC(O)CH$_3$, $R_{31}$ is —CH$_3$, and $R_1$ and $R_2$ are hydrogen).

Refer to Chart A (conversion of A-3 to A-4).

A solution of 0.55 g (1.45 mmol) of the piperidinol of Example 2, Part A above, 1 ml of triethylamine, 10 mg of 4-(dimethylamino)pyridine and 2 ml of acetic anhydride in 10 ml of methylene chloride is stirred at ambient temperature for 48 hr. The solution is washed with a 5% aqueous sodium hydroxide solution, twice with water, once with brine, dried over sodium sulfate and concentrated in vacuo to yield 0.7 g of a yellow oil.

The oil is chromatographed on 50 g of Silica Gel 60 ® and eluted with 4% methanol-chloroform mixture. The eluant from fractions 40 through 65 contains 0.4 g of pure subtitled free base product.

The 0.4 g of product is treated with ethereal hydrochloric acid and the precipitated salt is crystallized from an ethanol-diethyl ether mixture to afford 0.33 g (42%) of the subtitled salt product, a white powder with a melting point of 217°–219°. IR (Nujol) yields peaks at 1733 and 1766 cm$^{-1}$. NMR (DMSOd$_6$, δ) yields peaks at 1.75, 2.1, 2.6, 2.6–3.6, 7.2–7.75, and 11.2. The mass spectrum reveals an ion at m/e 402.

Anal. Calcd. for $C_{26}H_{30}N_4O_4$.2HCl: MW 535.48: C, 58.31; H, 6.02; N, 10.46. Found: C, 58.10; H, 6.05; N, 10.43.

PART C

4-[4-(3-hydroxyphenyl)-5-methyl-4H-1,2,4-triazol-3-yl]-1-(2-phenylethyl)-4-piperidinol, acetate (ester), dihydrochloride (Formula Ia: $X_1$ is m—OH, $Y_1$ is H, $R_3$ is OC(O)CH$_3$, $R_{31}$ is —CH$_3$, and $R_1$ and $R_2$ are hydrogen).

A mixture of 0.25 g (0.46 mmol) of the diacetate salt of Part B above and 1 g of potassium carbonate in 5 ml of methanol and 5 ml of water is stirred at ambient temperature for 20 hr. The mixture is extracted three times with chloroform and the chloroform extracts are washed with water, brine, dried over sodium sulfate and concentrated in vacuo at 45° C. to yield 0.17 g of oil.

The oil is dissolved in ethanol and treated with hydrochloric acid in diethyl ether. The precipitate is recystallized from ethanol-diethyl ether mixture to afford 0.13 g of the titled product with a melting point of 231°–235°. The IR (Nujol) spectrum reveals a peak at 1739 cm$^{-1}$. The mass spectrum reveals ions at m/e 360, 60, 58, 104, 228, 271, 91, 105, 148, 269, and 65.

Anal. Calcd. for $C_{24}H_{28}N_4O_3$.2HCl, m.w. 493.43: C, 58.42; H, 6.13; N, 11.36. Found: C, 58.64; H, 6.41; N, 11.36.

EXAMPLE 3

(3α,4α)-3-Methyl-4-(5-methyl-4-phenyl-4H-1,2,4-triazol-3-yl)-1-(2-phenylethyl)-4-piperidinol, acetate (ester), dihydrochloride, isomer A (Formula Ia: $R_{31}$ is methyl, $R_3$ is OC(O)CH$_3$, $R_1$ is methyl cis to $R_3$, $R_2$ is H, and $X_1$ and $Y_1$ are H).

PART A (3α, 4α)-3-Methyl-4-(5-methyl-4-phenyl-4H-1,2,4-triazol-3-yl)-1-(phenylmethyl)-4-piperidinol, isomer A and (3α,4β)-3-methyl-4-(5-methyl-4-phenyl-4H-1,2,4-triazol-3-yl)-1-(phenylmethyl)-4-piperidinol, isomer B (Formula Ia: $R_{31}$ is methyl, $R_3$ is OH, $R_1$ is methyl, $R_2$ is H, and $X_1$ and $Y_1$ are H).

The amino ester is prepared according to a similar procedure by Beckett, et al., (J. Med. and Pharm. Chem. 1, p. 37 (1959)). A solution of 161 ml (1.5 mole) of methyl methacrylate in 50 ml of methanol and 100 g (0.93 mole) of benzylamine is stored at room temperature for 12 days. The methanol and excess reagents are removed in vacuo at 40°.

The remaining liquid is distilled under high vacuum; bp 112°–114° (9 mm Hg), to afford 106 g (55%) of colorless liquid 2-methyl-3-[(phenylmethyl)amino]propanoic acid, methyl ester. An NMR spectrum supports the desired product structure and TLC analysis indicates one homogenous spot, $R_f$ 0.66 (15% MeOH/CHCl$_3$).

A solution of 78.2 g (0.38 mole) of starting amino-ester from above, 70 ml (0.77 mole) of methyl acrylate and 1 ml of Triton B solution (N-benzyltrimethylammonium hydroxide) is refluxed for 3 days. TLC indicates no starting material remaining.

Distillation of the product under high vacuum affords 95.1% (85%) of colorless product, 3-[N-[2-(methoxycarbonyl)ethyl]-N-(phenylmethyl)amino]-2-methyl-propanoic acid, methyl ester, bp 140°–144° (0.8 mm Hg). An NMR spectrum supports the desired product structure.

A mixture of 70 g (0.24 mole) of amino-diester from above in 500 ml touene and 11.7 g (0.24 mole) of sodium hydride is refluxed in a nitrogen atmosphere for 3 h. The yellow mixture is cooled in an ice bath and acidified with dilute acetic acid. The phases are separated. The organic phase is concentrated in vacuo to afford 65 g of a yellow, oily keto-ester.

To the 65 g from above is added 300 ml of 20% aqueous hydrochloric acid and the mixture is slowly heated to reflux. After 1 hour carbon dioxide ebullition quelled. A ferric chloride test is positive. The yellow solution is refluxed for 2 hours; ferric chloride test is negative. The cooled solution is concentrated in vacuo at 70° to an oily hydrochloride which is basified with 10% aqueous sodium hydroxide. The liberated amine is extracted with chloroform and washed with water, brine, dried over sodium sulfate and concentrated in vacuo to 37.6 g (84.5%) of 1-(phenylmethyl)-3-methyl-4-piperidone as an amber oil.

The oil is distilled under high vacuum, bp 100° (0.1 mm Hg), to afford 30 g of colorless liquid. An NMR spectrum supports the desired product and TLC analysis indicates one homogenous spot, $R_f$=0.73 (20% MeOH/CHCl$_3$).

Refer to Chart A (conversion of A-1 to A-3 except that A-2 contains an N-benzyl group).

A solution of 7.96 g (0.05 mol) of 3-methyl-4-phenyl-4H-1,2,4-triazole (prepared as in Example 1, Part A of U.S. Pat. No. 4,338,453) in 350 ml of tetrahydrofuran at −78° C. under a nitrogen atmosphere is treated dropwise, via a syringe, with 35 ml (0.055 mol) of a 1.6N solution of n-butyllithium in hexane. After completing the addition the mixture is stirred for 15 min. A solution of 10.5 g (0.05 mol) of 1-(phenylmethyl)-3-methyl-4-piperidone in 50 ml of tetrahydrofuran is added via syringe rapidly into the mixture. The coolant is removed and the solution allowed to reach ambient temperature in 1.5 hr. The reaction is quenched with aqueous ammonium chloride and the solvents are evaporated in vacuo. The resulting mixture is partitioned between 5% aqueous sodium hydroxide and chloroform. The combined chloroform extracts are washed with water and brine, dried over sodium sulfate and concentrated in vacuo at 50° C. to yield 17.5 g of white solid. An NMR spectrum of a homogeneous deutrochloroform solution of the white mixture indicated a 1:1 ratio of isomeric products and trace amounts of starting materials present.

The solid mixture is dissolved in methanol-ethyl acetate mixture and allowed to crystallize. The first crop of 2.2 g contains an approximate 75:25 ratio of isomers. Recrystallization of the 2.2 g from methanol-acetone-hexane mixture affords 0.55 g of colorless needles of the titled isomer A ($R_f$=0.48), with a melting point of 228°–229°; and IR (Nujol) peak at 3201 cm$^{-1}$; NMR (CDCl$_3$, δ) peaks at 0.72, 1.7–2.7, 2.13, 3.35, 3.4, 7.2, and 7.6. The mass spectrum yields ions at m/e 362, 344, and 271.

Anal. Calcd. for C$_{22}$H$_{26}$N$_4$O, MW 362.48: C, 72.90; H, 7.23; N, 15.46. Found: C, 72.70; H, 7.33; N, 15.58.

A fourth crop of 1.5 g of crystals is obtained from the initial 17.5 g of crude reaction product. Recrystallization of this 90:10 isomer mixture from a methanol-hexane mixture affords 0.62 g of colorless prisms, the titled isomer B ($R_f$=0.61), with a melting point of 185°–187°; IR (Nujol) peak at 3243 cm$^{-1}$; NMR (CDCl$_3$ δ) peaks at 0.88, 1.3–2.9, 2.11, 2.95, 3.4, 7.24, and 7.45. The mass spectrum yields ions at m/e 362, 344, 271, and 202.

Anal. Calcd. for C$_{22}$H$_{26}$N$_4$O, MW 362.48: C, 72,90; H, 7.23; N, 15.46. Found: C, 72.82; H, 7.25; N, 15.43.

Additional quantities of each isomer are obtained from 3.6 g of 1:1 mixture of isomers separated by HPLC. Eluant from a 7:3 ratio of acetone-methanol mixture affords 1.25 g of isomer B and 0.6 g of isomer A.

Part B (3α,4α)-3-Methyl-4-(5-methyl-4-phenyl-4H-1,2,4-triazol-3-yl)-4-piperidinol, Isomer A.

To a solution of 1.0 g (2.76 mmole) of the (3α,4α)-amino alcohol, isomer A of Part A above, in 100 ml absolute ethanol containing 2 ml of approximately 4.5N methanolic hydrochloric acid solution is added 1 g of 10% palladium on carbon. The Parr bottle is charged with 50 psi of hydrogen. After 72 hours the mixture is filtered through a Celite pad and the clear filtrate is evaporated in vacuo to an oily hydrochloride salt. The amine free base is liberated with a 10% aqueous solution of sodium hydroxide and extracted twice into chloroform. The extracts are dried over sodium sulfate and concentrated in vacuo to afford 0.64 g (85%) of white solid. A thin-layer chromatography analysis indicated a new polar spot, $R_f$=0.04 (50% acetone-chloroform), and no starting n-benzyl compound. This product is used without further purification in the alkylation reaction to provide the corresponding 1-(2-phenylethyl) piperidinol compound.

PART C (3α,4α)-3-methyl-4-(5-methyl-4-phenyl-4h-1,2,4-triazol-3-yl)-1-(2-phenylethyl)-4-piperidinol, isomer a (formula ia: $r_{31}$ is methyl, $x_1$ and $y_1$ are hydrogen, $r_1$ is methyl cis to $r_3$, $r_2$ is hydrogen, and $r_3$ is hydroxy) (This is an alternative method to produce a Formula A-3 compound).

A mixture of 0.64 g (2.36 mmole) of the crude amino alcohol of Part B above, 0.48 g (2.6 mmole) of (2-bromoethyl)benzene, and 0.69 g (5 mmole) of potassium carbonate in 25 ml of ethanol is refluxed under a nitrogen atmosphere for 22 hours. The solvent is removed in vacuo. The residue is diluted with water and extracted thrice with chloroform. The extracts are washed with brine, dried over sodium sulfate and concentrated in vacuo to afford 0.84 g (94%) of the titled white solid. TLC yields an $R_f$ of 0.5 (50% acetone-chloroform). The NMR spectrum supports the desired product structure. This material is used without further purification to prepare the corresponding acetate (ester).

PART D $(3\alpha,4\alpha)$-3-Methyl-4-(5-methyl-4-phenyl-4H-1,2,4-triazol-3-yl)-1-(2-phenylethyl)-4-piperidinol, acetate (ester), dihydrochloride, isomer A (Formula Ia: $R_{31}$ is methyl, $R_3$ is OC(O)CH$_3$, $R_1$ is methyl cis to $R_3$, $R_2$ is H, and $X_1$ and $Y_1$ are H).

Refer to Chart A (conversion of A-3 to A-4).

A solution of 0.84 g of amino alcohol isomer A, from Part C above, 2 ml of acetic anhydride, 1 ml of triethylamine, and a micro spatula tipful (approximately 10 to 80 mg) of 4-(dimethylamino)pyridine in 20 ml of methylene chloride was stirred at ambient temperature, under a nitrogen atmosphere for 5 days. A comparison of TLC after 5 days indicates virtually all the starting material remains. After removing solvents in vacuo, treating with 3 ml pyridine and 3 ml acetic anhydride and purifying as in Example 4, Part C below, 0.4 g of oil is obtained. The oil is converted to its hydrochloric acid salt and recrystallization from methanol-diethyl ether mixtures affords 0.25 g of the titled white powder salt, melting point of 233°–235° C. (bubble, amber), IR (Nujol) peaks at 1741 cm$^{-1}$, NMR (free base, $\delta$) reveals peaks at 0.97, 1.70, 2.08, 2.0–2.9, 7.0–7.3, 7.3–7.7, NMR (DMSOd$_6$, HCl salt, $\delta$) 0.90, 1.60, 2.05, 2.6–3.4, 7.1–7.4, and 7.4–7.65. The mass spectrum yields ions at m/e 418, 327, 358, 267, and 226.

Anal. Calcd. for C$_{25}$H$_{30}$N$_4$O$_2$.2 HCl, MW 491.49; C, 61.10; H, 6.56; N, 11.40, Cl, 14.43. Found: C, 61.47; H, 6.71; N, 11.38; Cl, 13.14.

EXAMPLE 4

$(3\alpha,4\beta)$-3-Methyl-4-(5-methyl-4-phenyl-4H-1,2,4-triazol-3-yl)-1-(2-phenylethyl)-4-piperidinol, acetate (ester), monohydrochloride, sesquihydrate, isomer B (Formula Ia: $R_{31}$ is methyl, $R_3$ is OC(O)CH$_3$, $R_1$ is methyl trans to $R_3$, $R_2$ is H, and $X_1$ and $Y_1$ are H).

PART A $(3\alpha,4\beta)$-3-Methyl-4-(5-methyl-4-phenyl-4H-1,2,4-triazol-3-yl)-4-piperidinol, Isomer B.

Following the procedure of Example 3, Part B above, the $(3\alpha,4\beta)$amino alcohol, Isomer B, from Example 3, Part A, above is debenzylated to the corresponding secondary amino alcohol, which is used without purification in the alkylation reaction (Part B).

PART B $(3\alpha,4\beta)$-3-Methyl-4-(5-methyl-4-phenyl-4H-1,2,4-triazol-3-yl)-1-(2-phenylethyl)-4-piperidinol, Isomer B. (Formula Ia: $R_{31}$ is methyl, $X_1$ and $Y_1$ are hydrogen, $R_1$ is methyl trans to $R_3$, $R_2$ is hydrogen, and $R_3$ is hydroxy).

Following the procedure for the alkylation of isomer A set forth in Example 3, Part C, above, 0.60 g (2.21 mmole) of the $(3\alpha,4\beta)$ secondary amino-alcohol (Isomer B) from Part A above, 0.48 g (2.6 mmole) of (2-bromoethyl)benzene 0.7 g (5 mmole) of potassium carbonate in 25 ml of absolute ethanol affords after workup, 0.80 g (96%) of titled yellow product having an $R_F$ OF 0.6 (50% acetone/chloroform). The NMR spectrum supports the desired product structure. This product is used directly to prepare the corresponding acetate.

PART C $(3\alpha,4\beta)$-3-Methyl-4-(5-methyl-4-phenyl-4H-1,2,4-triazol-3-yl)-1-(2-phenylethyl)-4-piperidinol, acetate (ester), monohydrochloride, sesquihydrate, isomer B (Formula Ia: $R_{31}$ is methyl, $R_3$ is OC(O)CH$_3$, $R_1$ is methyl trans to $R_3$, $R_2$ is H, and $X_1$ and $Y_1$ are H).

Refer to Chart A (conversion of A-3 to A-4).

A solution of 0.83 g (2.2 mmol) of the $(3\alpha,4\beta)$-(2-phenylethyl)amino-alcohol, Isomer B, of Part B above, 2 ml of acetic anhydride, 1 ml of triethylamine, and a micro spatula tip full of 4-(dimethylamino)pyridine in 20 ml of methylene chloride is stirred for 5 days at ambient temperature, under a nitrogen atmosphere. TLC analysis (15% methanol in chloroform) indicates approximately a 60% conversion of starting material. The solvents are removed in vacuo and the residue is treated with 3 ml pyridine and 3 ml acetic anhydride and heated to 110° C. for 2 hr. The reaction is cooled and is concentrated in vacuo to yield a gummy, brown oil. The oil is dissolved in chloroform and is washed with cold 10% aqueous sodium hydroxide, water, and brine, and dried over sodium sulfate and concentrated in vacuo to yield 1 g of crude product. The 1 g of crude product is chromatographed over 30 g of Silica Gel 60. The eluant from 5% methanol-chloroform in fractions 21 through 40 are combined and concentrated in vacuo to afford 0.35 g of a light yellow oil.

The 0.35 g of oil in diethyl ether is treated with ethereal hydrochloric acid, and the precipitated salt is recrystallized from a methanol-diethylether mixture to afford 0.22 g of the titled powdered salt with a melting point of 183°–185° C. (bubbles, amber). The IR (Nujol) spectrum reveals a peak at 1743 cm$^{-1}$. The NMR (CDCl$_3$, free base, $\delta$) reveals peaks at 0.94, 1.79, 2.11, 1.8–2.9, 6.9–7.3 and 7.3–7.6. The NMR (DMSOd$_6$-HCl-salt, $\delta$) reveals peaks at 1.06, 1.85, 2.15, 2.7–3.6, 7.1–7.3, 7.3–7.7 and 10.75. The mass spectrum reveals a molecular ion at m/e 418, with fragment ions at m/e 358, 327, 267, and 226.

Anal. Calcd. for C$_{25}$H$_{30}$N$_4$O$_2$.HCl.1.25 H$_2$O, MW 477.54; C, 62.88; H, 7.02; N, 11.73; Cl, 7.42. Found: C, 62.54; H, 6.58; N, 11.39; Cl, 8.93.

EXAMPLE 5

$(3\alpha,4\beta)$-4-(5-Methyl-4-phenyl-4H-1,2,4-triazol-3-yl)-1-(2-phenylethyl)-3-(2-propenyl)-4-piperidinol, acetate (ester), sesquihydrochloride, faster moving isomer B (Formula Ia: $R_{31}$ is methyl, $X_1$ and $Y_1$ are H, $R_1$ is CH$_2$=CH—CH$_2$— trans to $R_3$, $R_3$ is —OC(O)CH$_3$, $R_2$ is H)

PART A $(3\alpha,4\beta)$-4-(5-Methyl-4-phenyl-4H-1,2,4-triazol-3-yl)-1-(2-phenylethyl)-3-(2-propenyl)-4-piperidinol, faster moving (isomer B) and $(3\alpha,4\alpha)$-4-(5-methyl-4-phenyl-4H-1,2,4-triazol-3-yl)-1-(2-phenylethyl)-3-(2-propenyl)-4-piperidinol, slower moving (isomer A) (Formula Ia:

$R_{31}$ is methyl, $X_1$ and $Y_1$ are H, $R_1$ is $CH_2=CH-CH_2-$ trans to $R_3$, $R_3$ is $-OH$, $R_2$ is H).

Following a similar procedure according to Bell, et al., (J. Med. Chem. 16, 203 (1973)) an anhydrous solution of p-toluenesulfonic acid in toluene is prepared by refluxing 48.3 g (0.25 mole) of paratoluene-sulfonic acid monohydrate (TsOH.H$_2$O) in 400 ml of toluene with a Dean-Stark trap until 4.6 ml of water is collected. To the above cooled solution is added 50 g (0.25 mole) of 1-(β-phenethyl)-4-piperidone, 26.1 g (0.25 mole) of 2,2-dimethoxypropane and 32 g (0.55 mole) of allyl alcohol. The mixture is heated and refluxed under a jacketed Vigreux, 12 cm column fitted with a distillation head. The head temperature is maintained between 50° and 60° C. until about 20 ml of acetone is collected, then an additional 20 ml of distillate is collected up to 70° C. The reaction vessel is allowed to cool overnight at room temperature. The resulting brown residue is diluted with ether, filtered and washed with ether. The brown salt is vacuum dried at 50° C. to afford 103 g of crude product, 4,4-bis(2-propenyloxy)-1-(2-phenylethyl)-piperidinium-p-toluenesulfonate. This material is used directly in the following rearrangement reaction.

A suspension of the 103 g of crude salt from above in 300 ml of toluene containing about 0.5 g of TsOH.H$_2$O is heated under a 12.5 cm Vigreux column maintaining a head temperature between 90° and 98° C. until about 50 ml of allyl alcohol and toluene are collected. Then distillate is collected up to 110° C. The reaction is cooled to room temperature and water is added. The toluene is removed; the aqueous layer is chilled in an ice bath and basified with 20% aqueous sodium hydroxide. The liberated amine is extracted twice with ether. The ether extracts are washed with water, brine, dried over sodium sulfate and concentrated in vacuo at 50° C. to afford 65 g of dark brown oil.

The oil is distilled twice under reduced pressure, bp 117° (0.1 mm Hg) to afford 35 g (58%) of colorless product, 1-(2-phenylethyl)-3-(2-propenyl)-4-piperidinone. An NMR spectrum supports the desired product structure and also shows a trace of the starting 4-piperidone present. A TLC analysis gives one major homogenous spot, R$_f$0.4 (50% EtOAc/hexane) and a very faint spot of R$_f$0.2.

Refer to Chart A (conversion of A-1 to A-3).

To a stirred mixture of 5.0 g (0.031 mol) of 3-methyl-4-phenyl-4H-1,2,4-triazole in 350 ml of tetrahydrofuran at −78° C. (dry ice-isopropanol bath) under an atmosphere of nitrogen is added via syringe dropwise 22 ml (0.034 mol) of 1.55N n-butyllithium in hexane. The resulting slurry is stirred for 5 min between −78° and −60° C. A solution of 8.6 g (0.035 mol) of 1-(2-phenylethyl)-3-(2-propenyl)-4-piperidinone in 50 ml of tetrahydrofuran is then added dropwise into the reaction mixture at −78° C. within 3 min. The coolant is removed and the reaction flask is allowed to warm to approximately 20° C. The reaction is quenched with water and the solvents are removed in vacuo. The aqueous mixture is extracted with chloroform and the phases separated. The chloroform phase is washed with water (twice) and brine, dried over sodium sulfate and concentrated in vacuo at 50° C. to yield a white solid.

The solid is dissolved with a mixture of ethyl acetate-methanol-hexane and allowed to crystallize overnight. The first (5.5 g) and the second (4.5 g) crops are combined and recrystallized from a methanol-acetone mixture to afford a combined first and second crop of 6.8 g of colorless crystals of the titled (3α,4α)-isomer A with a melting point of 199°–201° C. TLC yields R$_f$ of 0.54 (50% methanol-50% acetone) (Isomer A, more polar, allyl cis to OH); and IR (Nujol) peak at 3207 cm$^{-1}$; NMR (CDCl$_3$ δ) peaks at 1.6–2.1, 2.13, 2.2–2.8, 3.72, 4.7–4.95, 5.2–5.8, 7.1–7.4 and 7.45–7.65. The mass spectrum yields ions at m/e 402, 384, 311, 152, 160, 312, 110 and 202.

Anal. Calcd. for C$_{25}$H$_{30}$N$_4$O, MW 402.55: C, 74.59; H, 7.51; N, 13.92. Found: C, 74.30; H, 7.36; N, 13.93.

The mother liquors from the ethyl acetate-methanol-hexane crystallizations are concentrated in vacuo, and the residue is crystallized from an ethyl acetate-hexane mixture to afford 2.0 g of colorless crystals of the titled (3α,4β)-isomer B, with a melting point of 193°–194° C.; and R$_f$ of 0.61 (50% methanol-50% acetone) (Isomer B, less polar, allyl trans to OH); IR (Nujol) peaks at 3238 cm$^{-1}$. The NMR (CDCl$_3$ δ) shows peaks at 1.2–2.25, 2.15, 2.28, 2.3–2.9, 4.65–4.95, 5.15–5.75, 7.1–7.35 and 7.4–7.6; and mass spectrum yields ions at m/e 402, 384, 311, 152, 312, 160, 110, and 202.

Anal. Calcd. for C$_{25}$H$_{30}$N$_4$O, MW 402.55: C, 74.59; H, 7.51; N, 13.92. Found: C, 74.38; H, 7.98; N, 13.99.

The total chemical yield is 11.7 g (93%). The pure less polar (3α,4β)-isomer B accounts for 2.35 g, the pure more polar (3α,4β)-isomer A accounts for 6.8 g, and a 1:1 mixture of isomers A and B accounts for 2.4 g. The ratio of the more polar to less polar isomer is approximately 7:3.

PART B (3α,4β)-4-(5-Methyl-4-phenyl-4H-1,2,4-triazol-3-yl)-1-(2-phenylethyl)-3-(2-propenyl)-4-piperidinol, acetate (ester), sesquihydrochloride, faster moving isomer B (Formula Ia: $R_{31}$ is methyl, $X_1$ and $Y_1$ are H, $R_1$ is $CH_2=CH-CH_2-$ trans to $R_3$, $R_3$ is $-OC(O)CH_3$, $R_2$ is H)

Refer to Chart A (conversion of A-3 to A-4).

A solution of 1.0 g (2.5 mmol) of (3α,4β)-aminoalcohol, isomer B from Part A above, 2 ml of acetic anhydride and 2 ml of dry pyridine in 6 ml of toluene is refluxed in an atmosphere of nitrogen for 18 hr. The cooled solution is concentrated in vacuo to yield a dark oil. The oil is dissolved in chloroform and washed with a 5% solution of aqueous sodium hydroxide, washed twice with water, once with brine, dried over sodium sulfate and concentrated in vacuo to yield 1.8 g of a dark oil.

The 1.8 g of oil is chromatographed on 100 g of Silica Gel 60, eluting with a 3% methanol-chloroform mixture. Eluant from fractions 28–60 are combined and concentrated in vacuo to afford 0.93 g of a yellow, oily product.

The 0.93 g of free base is treated with hydrochloric acid in diethyl ether and the resultant hydrochloride salt is recrystallized from a methanol-diethyl ether mixture to afford a first crop of 0.63 g (52%) of the titled white powder salt, which shrinks at 164° C. and melts 178°–182° C. (viscous, water clear). The IR (Nujol) spectrum shows a peak at 1750 cm$^{-1}$. NMR (CDCl$_3$, free base, δ) reveals peaks at 1.80, 2.11, 1.5–3.0, 4.75–5.10, 5.20–5.80, 7.0–7.4, and 7.4–7.7. NMR (DMSOd$_6$), HCl-salt, δ, peaks observed are 1.90, 2.21, 2.1–3.4, 5.1–5.35, 5.3–5.5, 7.1–7.4, 7.4–7.6 and 11.3. The mass spectrum yields ions at m/e 444, 401, 353, 343, 384, 293, and 252. High resolution mass spect.; Calcd. for C$_{27}$H$_{32}$N$_4$O$_2$=444.2525; Found: 444.2518.

Anal. Calcd. for $C_{27}H_{32}N_4O_2 \cdot HCl \cdot CH_3OH \cdot 0.5H_2O$; MW 518.10: C, 64.91; H, 7.39; N, 10.81; Cl, 6.84. Found: C, 64.46; H, 7.05; N, 10.95; Cl, 9.28.

A 40 mg sample of this product was converted to the free base with 10% aqueous sodium hydroxide and treated with one equivalent of p-toluenesulfonic acid to provide a colorless prism for x-ray analysis which unambiguously established the structure of this titled product with the $(3\alpha,4\beta)$ stereochemistry.

EXAMPLE 6

$(3\alpha,4\beta)$-4-(5-methyl-4-phenyl-4H-1,2,4-triazol-3-yl)-1-(2-phenylethyl)-3-(2-propenyl)-4-piperidinol, acetate (ester), sesquihydrochloride, hemihydrate, slower moving isomer A (Formula Ia: $R_{31}$ is methyl, $X_1$ and $Y_1$ are H, $R_1$ is $CH_2=CH-CH_2-$ cis to $R_3$, $R_3$ is $-OCOCH_3$, $R_2$ is H).

Refer to Chart A (conversion of A-3 to A-4).

Following the procedure of Example 5, Part B, the titled compound is prepared from 1.7 g (4.2 mmol) of the $(3\alpha,4\alpha)$-amino-alcohol, isomer A of Example 5, Part A, 5 ml of acetic anhydride, and 5 ml of pyridine to afford 1.2 g of oily acetate.

Conversion of the free base to the hydrochloride salt affords two crops of 0.78 g of the titled white powder salt with a melting point of 180°–181°. IR (Nujol) reveals a peak at 1738 cm$^{-1}$. The NMR (CDCl$_3$, free base, $\delta$) reveals peaks at 1.76, 2.09, 2.0–3.0, 4.80–5.10, 5.3–5.9, 7.0–7.4 and 7.4–7.65. The NMR (DMSOd$_6$, HCl salt, $\delta$) reveals peaks at 1.73, 2.11, 2.7–3.8, 5.35–5.9, 7.2–7.5, 7.5–7.75 and 11.4. The mass spectrum yields ions at m/e 444, 401, 353, 343, 344, 384, 354, 293, 160, 110, and 252.

Anal. Calcd. for $C_{27}H_{32}N_4O_2 \cdot 1.5HCl \cdot 0.5H_2O$; MW 508.29; C, 63.83; H, 6.84; N, 11.02; Cl, 10.46. Found: C, 63.69; H, 6.70; N, 10.96; Cl, 10.39.

EXAMPLE 7

4-(5-Methyl-4-phenyl-4H-1,2,4-triazol-3-yl)-1-(2-phenylethyl)-4-piperidinol, formate (ester) (Formula Ia: $R_{31}$ is methyl, $X_1$ and $Y_1$ are hydrogen, $R_3$ is $-OCOH$, and $R_1$ and $R_2$ are hydrogen)

Refer to Chart A (conversion of A-3 to A-4). The mixed anhydride is prepared according to Mehlenbacher, Org. Analysis, 1, 37 (1953) by slow addition of 5 ml of 97% formic acid to 10 ml of acetic anhydride at 0°, and then warming to 50° C. for 15 minutes.

A solution of 0.7 g of the starting piperidinol of Example 15, Part A below in 2 ml of dry pyridine at 0° C. was treated with 2 ml of the mixed anhydride reagent from above. The coolant is removed and the solution allowed to warm to ambient temperature for 18 hours. The reaction solution is poured into a cold saturated sodium bicarbonate solution and extracted twice with chloroform. The combined chloroform extracts are washed twice with water, dried over sodium sulfate and concentrated in vacuo to 0.65 g of oil.

The 0.65 g of oil is chromatographed on 50 g of Silica Gel 60 which is eluted with 10% methanol-chloroform mixture to afford 0.3 g of desired titled product. Crystallization from diethyl ether affords a first crop of 0.1 g as colorless clusters with a melting point of 140°–141° C. (water-clear melt). The IR, mass spectrometry, and NMR spectra support the desired product structure.

Anal. Calcd. for $C_{23}H_{26}N_4O_2$, mw 390.49: C, 70.74; H, 6.71; N, 14.35. Found: C, 70.23; H, 6.65; N, 14.40.

EXAMPLE 8

4-[4-(2-fluorophenyl)-5-methyl-4H-1,2,4-triazol-3-yl]-1-(2-phenylethyl)-4-piperidinol, acetate (ester) (Formula Ia: $R_{31}$ is methyl, $X_1$ is 2-fluoro, $Y_1$ is hydrogen, $R_1$ and $R_2$ are hydrogen, and $R_3$ is $OCOCH_3$)

PART A

4-[4-(2-fluorophenyl)-5-methyl-4H-1,2,4-triazol-3-yl]-1-(2-phenylethyl)-4-piperidinol.

Using the method of Example 1, Part A of U.S. Pat. No. 4,338,453, 2-fluorophenyl isothiocyanate and acethydrazide are reacted to produce 4-(2-fluorophenyl)-5-methyl-4H-1,2,4-triazole-3-thiol (mp 236°–237° C., C:H:N:S:F ratio 51.69:3.86:20.10:15.84:9.10) which is converted to 4-(2-fluorophenyl)-3-methyl-4H-1,2,4-triazole (mp 119°–120° C., C:H:N:F ratio 61.28:4.83:23.58:10.42).

Refer to Chart A (conversion of A-1 to A-3)

Using the method of Example 1, Part A above 4-(2-fluorophenyl)-5-methyl-4H-1,2,4-triazole is converted to its anion and reacted with 1-($\beta$-phenethyl)-4-piperidinone to produce the subtitled compound, mp 172°–174° C. and C:H:N:F ratio 69.05:6.55:14.51:5.22.

PART B

4-[4-(2-fluorophenyl)-5-methyl-4H-1,2,4-triazol-3-yl]-1-(2-phenylethyl)-4-piperidinol, acetate (ester) (Formula Ia: $R_{31}$ is methyl, $X_1$ is 2-fluoro, $Y_1$ is hydrogen, $R_1$ and $R_2$ are hydrogen, and $R_3$ is $OCOCH_3$).

Refer to Chart A (conversion of A-3 to A-4).

A solution of 1.0 g (2.6 mmole) of the amino-alcohol from Part A above, 2 ml of acetic anhydride, 2 ml of triethylamine and approximately 20 mg of 4-dimethylamino pyridine in 5 ml of methylene chloride is stirred at ambient temperature under a nitrogen atmosphere for 72 hours. The resultant red colored solution is poured onto a 5% aqueous sodium hydroxide solution. The phases are separated. The organic phase is washed with water, brine, dried over sodium sulfate and concentrated in vacuo to 1.2 g of crude product.

The crude product is chromatographed on 50 g Silica Gel 60 ® and eluted with a 5% methanol-chloroform mixture to afford 0.82 g of crude solid product. Crystallization from an ethyl acetate-hexane mixture affords a first crop of 0.58 g (53%) of slightly yellow crystals of the titled product, melting point of 157°–159° C.

Anal. Calcd. for $C_{24}H_{27}FN_4O_2$; mw 422.51: C, 68.22; H, 6.44; N, 13.26; F, 4.50. Found: C, 68.05; H, 6.77; N, 12.93; F, 4.67.

EXAMPLE 9

4-[4-(2,6-dimethylphenyl)-5-methyl-4H-1,2,4-triazol-3-yl]-1-(2-phenylethyl)-4-piperidinol, acetate (ester) (Formula Ia: $R_{31}$ is methyl, $X_1$ is 2-methyl, $Y_1$ is 6-methyl, $R_1$ and $R_2$ are hydrogen, and $R_3$ is $OCOCH_3$).

PART A

4-[4-(2,6-dimethylphenyl)-5-methyl-4H-1,2,4-triazol-3-yl]-1-(2-phenylethyl)-4-piperidinol.

Using the method of Example 1, Part A of U.S. Pat. No. 4,338,453, 2,6-dimethylphenyl isothiocyanate and acethydrazide are reacted to produce 4-(2,6-dimethylphenyl)-5-methyl-4H-1,2,4-triazole-3-thiol which is converted to 4-(2,6-dimethylphenyl)-3-methyl-4H-1,2,4-triazole. This triazole (1.87 g 0.01 mole) in 100 ml of tetrahydrofuran at $-60°$ C. bath temperature is reacted with 6.9 ml of 1.6N n-butyllithium in hexane. The resulting mixture is stirred for fifteen minutes. Then using the procedure of Example 1, Part A above, this anion is reacted with 1-(β-phenethyl)-4-piperidinone to produce the product, which is recrystallized from ethyl acetate-hexane to give the subtitled product, mp 189°–192° C., with a C:H:N ratio of 73.30:7.77:14.27.

PART B

4-[4-(2,6-dimethylphenyl)-5-methyl-4H-1,2,4-triazol-3-yl]-1-(2-phenylethyl)-4-piperidinol, acetate (ester) (Formula Ia: $R_{31}$ is methyl, $X_1$ is 2-methyl, $Y_1$ is 6-methyl, $R_1$ and $R_2$ are hydrogen, and $R_3$ is $OCOCH_3$).

Refer to Chart A (conversion of A-3 to A-4). Using an esterification procedure described herein the alcohol from Part A above is converted to the subtitled acetate ester (which is recrystallized from acetone-hexane), mp 138°–140° C., C:H:N ratio 72.20:7.44:12.95 (MW 432.58).

EXAMPLE 10

4-[4-(2,6-dimethylphenyl)-5-methyl-4H-1,2,4-triazol-3-yl]-1-(2-phenylethyl)-4-piperidinol, propanoate (ester), and its monohydrobromide (Formula Ia: $R_{31}$ is methyl, $X_1$ is 2-methyl, $Y_1$ is 6-methyl, $R_1$ and $R_2$ are hydrogen, and $R_3$ is $OCOCH_2CH_3$).

Refer to Chart A (conversion of A-3 to A-4). Using an esterification procedure described herein the alcohol from Example 9, Part A above is converted to the titled propanoate ester (which is recrystallized from ethanol-water), mp 207°–209° C., with a C:H:N:Br ratio of 61.05:6.79:10.20:15.00 (MW 527.53).

EXAMPLE 11

4-[4-(2,6-diethylphenyl)-5-methyl-4H-1,2,4-triazole-3-yl]-1-(2-phenylethyl)-4-piperidinol, acetate (ester) and its monohydrochloride, and its monohydrate (Formula Ia: $R_{31}$ is methyl, $X_1$ is 2-ethyl, $Y_1$ is 6-ethyl, $R_1$ and $R_2$ are hydrogen, and $R_3$ is $OCOCH_3$).

Refer to Chart A for conversion of A-1 to A-4. Proceeding according to Example 9 above and starting with 2,6-diethylphenyl isothiocyanate and acethydrazide the following compounds are prepared in turn:

- 4-(2,6-diethylphenyl)-5-methyl-4H-1,2,4-triazole-3-thiol, mp 182°–183.5° C. (from ethyl acetate-hexane), C:H:N:S ratio 63.36:6.93:16.95:13.13;
- 4-(2,6-diethylphenyl)-3-methyl-4H-1,2,4-triazole, mp 58°–60° C. (from pentane), C:H:N ratio 72.52:7.95:19.66;
- 4-[4-(2,6-diethylphenyl)-5-methyl-4H-1,2,4-triazol-3-yl]-1-(2-phenylethyl)-4-piperidinol, mp 188°–189° C. (from ethyl acetate), C:H:N ratio 74.62:8.11:13.43 (MW 418.59);
- 4-[4-(2,6-diethylphenyl)-5-methyl-4H-1,2,4-triazol-3-yl]-1-(2-phenylethyl)-4-piperidinol, acetate (ester) as the monohydrochloride hydrate, mp 121°–123° C. (from ethanol-diethyl ether) with a C:H:N:Cl ratio 65.72:7.28:10.86:7.33.

EXAMPLE 12

1-(2-Phenylethyl)-4-(4-phenyl-4H-1,2,4-triazol-3-yl)-piperidine (Formula Ia: $R_{31}$ is hydrogen, $X_1$ and $Y_1$ are hydrogen, $R_1$, $R_2$ and $R_3$ are hydrogen). Refer to Chart B. (Conversion of B-1 to B-7).

PART A

4-Phenyl-5-(4-pyridinyl)-4H-1,2,4-triazole-3-thiol

A one liter round bottomed flask, fitted with a reflux condenser, nitrogen inlet and magnetic stirrer bar, is charged with 40.5 g (0.30 mol) of phenyl isothiocyanate and 41.845 g (0.30 mol) of isonicotinic acid hydrazide in 300 ml of absolute ethanol. The mixture is heated to reflux for 3 hours. The resulting solid is filtered and washed with ethanol and then added to an aqueous solution of sodium hydroxide (prepared by dissolving 16.8 g, 0.42 mol, of sodium hydroxide in 240 ml of water). The mixture is heated to reflux for 5 hours and then stirred at ambient temperature for 18 hours. The solution is treated with 100 ml of distilled water to dissolve the gel which has formed. The solution is made acidic (to pH 2) with concentrated HCl and cooled with ice. The solid is filtered, taken up in 600 ml of warm absolute ethanol and filtered again to afford approximately 70 g (92%) of slightly wet titled product with a melting point of 288°–290° C. IR (nujol shows a peak at 1900 $cm^{-1}$; UV (95% ethanol) shows peaks at 257 nm and 317 nm; NMR (DMSO-d6 δ) 8.5 and 7.2–7.6; the mass spectra shows a strong molecular ion peak at m/e 254, with fragment ions at 253, 195 and 149.

Anal. Calcd. for $C_{13}H_{10}N_4S$, mw 254.26: C, 61.41; H, 3.96; N, 22.04; S, 12.59. Found: C, 61.23; H, 4.05; N, 22.20; S, 12.59.

PART B 4-(4-Phenyl-4H-1,2,4-triazol-3-yl)-pyridine

The triazolethiol of Part A (17.0 g, 66.9 mmol) is cautiously added, in portions, to 48 ml of a 20% nitric acid solution heated on a steam bath. After the addition is complete (15 minutes) the brown solution is heated an additional ½ hour, cooled, and quenched in cold, aqueous ammonium hydroxide. The resulting tan solid is filtered to give 19.2 g of crude powder which is dissolved in hot methanol, treated with charcoal and dried over sodium sulfate and crystallized from methanol/ethyl acetate mixtures to afford beautiful prisms, (12.16 g, 81.8%, in two crops), melting point 224°–227° C.: spectral data is as follows: IR (nujol) peaks at 3122 and 3052 $cm^{-1}$; UV (95% ethanol) peaks at 244 nm; NMR ($CDCl_3$ δ) peaks at 8.59, 8.37, and 7.2–7.6; mass spectrum shows a strong molecular ion peak at m/e 222, with a fragment ion at 221.

Anal. Calcd. for $C_{13}H_{10}N_4$, mw 222.25: C, 70.25; H, 4.54; N, 25.21. Found: C, 70.22; H, 4.54; N, 25.21.

PART C 4-(4-Phenyl-4H-1,2,4-triazol-3-yl)-piperidine

The starting material from Part B (8.92 g, 40.1 mmol) dissolved in 80 ml acetic acid is treated with 1.6 g of platinum oxide and hydrogenated in a Parr Bomb at 51.5 psi initial pressure. The pressure drops to 39.5 psi after 64 hours, but the reaction is continued for an additional 4 days (final pressure, 39.0 psi). The crude reaction mixture, including catalyst, is quenched in cold aqueous sodium hydroxide, treated with chloroform, and both layers are filtered through celite to remove platinum. The organic layer is separated, dried over sodium sulfate, and concentrated in vacuo to 10.79 g of solid which is crystallized from methanol/ethyl acetate mixtures (after Darco decolorizing carbon treatment) to afford 8.67 g (94.7%) of needles, in two crops, metling point 165°–169° C.: IR (nujol) 3291 $cm^{-1}$; UV (95% ethanol) 256 nm, 257 nm with sh at 261, 264, 280, and 310 nm; NMR ($CDCl^3$) 8.15, 7.2–7.6, 1.7–3.2; mass spectrum shows a weak molecular ion peak at m/e 228 with a strong fragment ion at m/e 172.

Anal. Calcd. for $C_{13}H_{16}N_4$, mw 228.30: C, 68.39; H, 7.07; N, 24.55. Found: C, 68.08; H, 7.02; N, 24.10. An undried sample analyzed correctly for a ½ methanol solvate.

PART D 1-(2-Phenylethyl)-4-(4-phenyl-4H-1,2,4-triazol-3-yl)-piperidine

The starting triazolyl piperidine from Part C above (2.28 g, 10.0 mmol) and beta-phenylethyl bromide (2.04 g, 10.0 mmol) are dissolved in 30 ml of absolute ethanol and treated with potassium carbonate (1.93 g, 14.0 mmol). The mixture is refluxed for 24 hours, cooled, quenched in cold aqueous 10% sodium hydroxide, and the product is extracted with chloroform. The chloroform layer was dried over sodium sulfate and concentrated in vacuo to a solid (3.42 g, crude) which crystallized from methanol/ethyl acetate mixtures to afford 0.97 g (29.2%) of colorless prisms, melting point 180°–182° C. A second crop weighed 1.04 g (31.3%): IR (nujol) 1596 cm$^{-1}$; UV (95% ethanol) 258 nm, with shoulders at 259 nm, 263 nm and 266 nm; NMR (CDCl$_3$, $\delta$) 8.15, 7.0–7.6, and 1.7–3.2; mass spectrum: strong ion peak at m/e 333, with fragment ions at 241 and 57.

Anal. Calcd. for C$_{21}$H$_{24}$N$_4$, mw 332.44: C, 75.87; H, 7.28; N, 16.86. Found: C, 76.00; H, 7.25; N, 16.92.

EXAMPLE 13

4-(5-Methyl-4-phenyl-4H-1,2,4-triazol-3-yl)-1-(2-phenylethyl)piperidine (Formula Ia: R$_{31}$ is methyl, X$_1$ and Y$_1$ are hydrogen, and R$_1$, R$_2$ and R$_3$ are hydrogen). and 4-(5-ethyl-4-phenyl-4H-1,2,4-triazol-3-yl)-1-(2-phenylethyl)-piperidine (Formula Ia: R$_{31}$ is ethyl, X$_1$ and Y$_1$ are hydrogen, and R$_1$, R$_2$ and R$_3$ are hydrogen).

Refer to Chart B (conversion of B-7 to B-8). The starting piperidine from Example 12, Part D above (1.328 g, 4.00 mmol), suspended in 24 ml of tetrahydrofuran in a 100 ml round bottomed flask with side-arm and rubber stopper, magnetic stirrer bar and nitrogen inlet, is treated rapidly, at 0° C., with two equivalents of a 1.6M solution of n-butyllithium, followed 30 seconds later by a tetrahydrofuran solution of methyl iodide (1.17 g, 8.24 mmol) in 2.0 ml of tetrahydrofuran. The solution is stirred for ½ hour at 0° C., then quenched in a cold aqueous 10% sodium hydroxide solution. The organic products are extracted with CHCl$_3$, which is dried (Na$_2$SO$_4$), and concentrated in vacuo to 1.44 g of oil, which solidifies on standing. Thin layer chromatography using Silica Gel, 10% methanol/90% CHCl$_3$, containing one drop of a concentrated NH$_4$OH solution) reveals the formation of at least three new products. These are separated by chromatography over Silica gel 60 (150 g) by eluting with 1 liter of 2% methanol/98% CHCl$_3$, and 1 liter of 4% methanol/96% CHCl$_3$, each containing 5 ml of a concentrated aqueous NH$_4$OH solution per liter. Following a 20 ml forerun. 20 ml fractions are collected.

Fractions 65–80 contain 0.579 g of oil which crystallizes when triturated with diethyl ether. This material is crystallized slowly from ethyl acetate/diethyl ether mixtures to afford 0.169 g of the 5-ethyl adduct. The analytical sample has a melting point of 110°–112° C.: IR (Nujol) 1597 and 1500 cm$^{-1}$; UV (95% ethanol) 258 nm, 262, and 267.5 nm; NMR (CDCl$_3$ $\delta$) 7.2–7.6, 1.8–3.2, and 1.20; mass spectrum, very weak M+1 ion at m/e 361 with a base peak at m/e 269.1721.

Anal. Calcd. for C$_{23}$H$_{28}$N$_4$, mw 360.49: C, 76.63; H, 7.83; N, 15.55. Found: C, 75.91; H, 7.82; N, 15.39.

Fractions 81–105 contain a solid which is crystallized twice from ethyl acetate/diethyl ether mixtures to afford 102 mg of the titled 5-methyl compound as a white powder with a melting point of 141–143: IR (Nujol) 1596, 1528, and 1505 cm$^{-1}$; NMR (CDCl$_3$, $\delta$) 7.4–7.6, 7.0–7.2, 2.22, and 1.5–3.0; mass spectrum shows a weak molecular ion at m/e 346.2136.

Anal. Calcd. for C$_{22}$H$_{26}$N$_4$, mw 346.47: C, 76.26; H, 7.56; N, 16.17. Found: C, 76.17; H, 7.68; N, 15.94.

EXAMPLE 14

1-(2-Phenylethyl)-4-(3-phenyl-4H-1,2,4-triazol-4-yl)piperidine (Formula Ib: R$_{31}$ is hydrogen, X$_1$ and Y$_1$ are hydrogen, and R$_1$ and R$_2$ are hydrogen). Refer to Chart C (conversion of C-1 to C-7).

PART A

N-($\beta$-phenylethyl)-4-amino-piperidine

Following the procedure of Lobbezoo, J. Med. Chem. 24:777 (1981). N-($\beta$-phenylethyl)-4-piperidinone (15.0 g, 74.0 mmol) dissolved in 200 ml of methanol containing 1 ml of a 4% thiophene in methanol solution is treated with benzyl amine (10.0 g, 93.0 mmol) and 2 g of 10% palladium-on-carbon in a Parr flask and hydrogenated for 18 hours (initial pressure, 26.5 psi, final pressure 22.0 psi). The catalyst is filtered and replaced with 2.0 g of fresh 10% palladium-on-carbon. The catalyst is filtered and replaced again with 4.8 g of fresh 10% palladium-on-carbon. The hydrogenation is followed over 3 days, at which point, hydrogen uptake ceases (initial pressure, 35 psi, final pressure, 29 psi). The catalyst is filtered through Celite and is washed with methanol. GLC analysis (2 ft SE-30, 100 C, 1 minute, programmed 20 C/minute rise to 250 C) indicated that 7% unreacted benzyl amine remained). This material nevertheless was used for subsequent experiments.

PART B 1-(2-Phenylethyl)-4-(3-phenyl-4H-1,2,4-triazol-4-yl)piperidine

4-Amino-1-(2-phenylethyl)piperidine (13.95 g, 68.3 mmol) is treated with dimethylformamide dimethylacetal (16.28 g, 136.6 mmol) and heated to reflux for 3 hours. The reaction solution is concentrated in vacuo to an oil which solidifies on standing, but is not recrystallized. A portion of this crude formamidine (7.77 g, 30.0 mmol) is dissolved in 36 ml of benzoic acid hydrazide (4.08 g, 30.0 mmol) and heated first for 14 hour at 55° C., then 4 hours at reflux. The solution is quenched in cold aqueous 10% NaOH, which is extracted with CHCl$_3$ and dried over Na$_2$SO$_4$. The organic layer is concentrated in vacuo to a dark oil which is chromatographed over 300 g of silica gel by eluting with 2 liters of 4% methanol/96% CHCl$_3$, containing 5 ml of aqueous concentrated NH$_4$OH/liter. Following a 300 ml forerun, 20 ml fractions are collected. The product is collected in fractions 61–84 and crystallized from ethyl acetate/Et$_2$O to afford 3.936 g (39.5% yield) of tan prisms. The analytical sample has a melting point of 124°–125° C.: IR (Nujol) 3031, and 2960 cm$^{-1}$; UV (95% ethanol) 227 nm; NMR (CDCl$_3$, $\delta$) 8.35, 7.54, 7.23, 4.0, 3.07, 2.70, and 2.04; mass spectra weak molecular ion at m/e 332 with a base peak at 241.

Anal. Calcd. for C$_{21}$H$_{24}$N$_4$, mw 332.44: C, 75.87; H, 7.28; N, 16.86. Found: C, 75.83; H, 7.40; N, 16.77.

EXAMPLE 15

4-(5-Methyl-4-phenyl-4H-1,2,4-triazol-3-yl)-1-(2-phenylethyl)-4-piperidinol, acetate (ester) (Formula Ia: R$_{31}$ is methyl, X$_1$ and Y$_1$ are hydrogen, R$_1$ and R$_2$ are hydrogen, and R₃ is —OCOCH₃); 4-(5-Methyl-4-phenyl-4H-1,2,4-triazol-3-yl)-1-(2-phenylethyl)-4-piperidinol, propanoate ester (Formula Ia: $R_{31}$ is methyl, $X_1$ and $Y_1$ are hydrogen, $R_1$ and $R_2$ are hydrogen, and $R_3$ is —OCOCH₂CH₃).

PART A 4-(5-Methyl-4-phenyl-4H-1,2,4-triazol-3-yl)-1-(2-phenylethyl)-4-piperidinol To a solution of 1.6 g of 3-methyl-4-phenyl-4H-1,2,4-triazole (10 mmol) in 15 ml of THF at −78° C. is added 7.0 ml of n-butyllithium (1.6N in hexane). The mixture is stirred for 50 minutes before a solution of 2.44 g of N-(2-phenylethyl)-4-piperidinone in 12 ml of THF is charged into the flask. After stirring for 30 minutes at −78° C. and then 1 hour at −20° C. the mixture is poured into cold water and is extracted three times with chloroform. The combined chloroform extracts are washed twice with water, brine, dried over sodium sulfate and concentrated in vacuo to yield an amber oil.

The oil is dissolved in ethyl acetate-hexane mixture and is allowed to crystallize. Recrystallization from a methanol-ethyl acetate-hexane mixture affords 1.9 g of prisms of the subtitled product with a melting point of 183°–184° C. (clear): IR (Nujol) 3180, 2780, 1600, 1580, 1540, 1515 and 1500 cm$^{-1}$; NMR (CDCl₃) δ 1.7–2.05, 2.14, 2.20–2.85 and 2.95; mass spectrum molecular ion peak at m/e 363 (very weak), with fragment ion peaks at m/e 271, 112, 160, 272 and 202.

Anal. Calcd. for C₂₂H₂₆N₄O mw 362.46: C, 72.90; H, 7.23; N, 15.46. Found: C, 73.08; H, 7.18; N, 15.40.

PART B 4-(5-methyl-4-phenyl-4H-1,2,4-triazol-3-yl)-1-(2-phenylethyl)-4-piperidinol, acetate (ester)

To a solution of 0.5 g of the product of Part A in 20 ml of methylene chloride and 3 ml acetic anhydride is added 50 mg of 4-(dimethylamino)pyridine (DMAP) and the mixture is refluxed for 18 hours.

The solution is diluted with water, and the phases are separated. The organic phase is washed with water, dried over sodium sulfate and concentrated in vacuo to give 0.46 g of crude product.

Crystallization from ethyl acetate-hexane gives 0.3 g of the desired subtitled ester with a melting point of 163°–164° C.

NMR (CDCl₃) δ 1.70, 2.15, 2.25–2.50, 2.55–2.95, and 7.0–7.65; mass spectral fragment ion peaks at 361, 344, 313, 253, 212 and 345.

Anal. Calcd. for C₂₄H₂₈N₄O₂, mw 404.52: C, 71.26; H, 6.98; N, 13.85. Found: C, 70.93; H, 6.94; N, 13.98.

PART C 4-(5-methyl-4-phenyl-4H-1,2,4-triazol-3-yl)-1-(2-phenylethyl)-4-piperidinol, propanoate (ester).

Using the procedure of Part B above, 0.62 g of the titled product ester are prepared from 1.0 g of the starting alcohol from Part A above, 2 ml of propionic anhydride and 0.45 g of DMAP. Spectral data support the proposed structure.

Anal. Calcd. for C₂₅H₃₀N₄O₂: mw 418.55: C, 71.74; H, 7.22; N, 13.39. Found: C, 71.42; H, 7.32; N, 13.56.

EXAMPLE 16

4-(3-Phenyl-4H-1,2,4-triazol-4-yl)-piperidine and its dihydrochloride.

PART A

1-Benzyl-4-piperidinone-oxime

Following a procedure of P. Brookes, et al., J. Chem. Soc., 3165 (1957), 1-benzyl-4-piperidinone (44.6 g, 0.234 mol) and hydroxylamine hydrochloride (14.0 g, 0.201 mol) are added to 140 ml of dry pyridine and the resulting mixture is heated to 100° C. in an oil bath for 3 hours. The resulting solid is cooled overnight, filtered and crystallized from 1 liter of ethanol. The product is collected as colorless needles, 38.17 g, in two groups with melting point of 225°–237° C., decomposed depending upon the rate of heating.

PART B

1-Benzyl-4-amino-piperidine

Following the procedure of Brookes, et al., the oxime hydrochloride salt from Part A above is suspended in hot absolute ethanol and treated with a solution of NaOEt prepared from Na (2.3 g, 0.10 mol) in 50 ml of absolute ethanol. The amorphous solid which forms is filtered. The mother liquor, containing the oxime free base is boiled on a steam bath while small pieces of Na (23.0 g, 1.0 g-atom) are added at a rate to prevent foaming. The addition takes 15 minutes. The mixture is heated an additional period until all the Na has reacted. Distilled water is then added to the reaction vessel (an Erlenmeyer flask) while the ethanol is removed by blowing a stream of nitrogen over the surface of the reaction solution. The flask is removed from the steam bath and permitted to cool. The product is isolated by extracting the aqueous layer with diethyl ether. The organic layer is dried (Na₂SO₄) and concentrated in vacuo to an oil, 16.8 g (88.4% yield). By GLC, this oil is 83% pure. The impurity is not characterized. This material is used for subsequent experiments.

PART C

N,N-Dimethyl-N'-(1-benzyl-piperidin-4-yl)-formamidine

The starting 4-amino-1-benzylpiperidine from Part B above (15.0 g, 78.8 mmol) is treated with dimethylformamide dimethylacetal (18.78 g, 157.6 mmol) and refluxed for 2 hours. The solution is permitted to cool overnight, then concentrated in vacuo to the product (15.5 g of oil, 83.2% yield), which solidifies on standing. A small portion crystallizes from hexane to afford colorless needles with a melting point of 61°–65° C.: NMR (CDCl₃ δ) 7.28, 3.49, 2.80, and 1.75–3.0; mass spectral molecular ion peak at m/e 245, with abundant fragment ions at m/e 200, 173, 172, 154, and 91.

Anal. Calcd. for C₁₅H₂₃N₃, mw 245.36: C, 73.42; H, 9.45; N, 17.13. Found: C, 73.02; H, 9.27; N, 16.96.

PART D

Benzoic acid, 2-[[[1-(phenylmethyl)-4-piperidinyl]imino]methyl]-hydrazide

The starting formamidine from Part C above (11.61 g, 47.3 mmol) dissolved in 28 ml of warm diglyme, is treated with a solution of benzoic acid hydrazide (6.44 g, 47.3 mmol) dissolved in 28 ml of warm diglyme. The solution is heated for 14 hours at 55° C. The resulting solid is filtered to afford 18.64 g of crude, "wet" amidrazone. Three grams of this material is saved and recrystallized from methanol/ethyl acetate mixtures to afford 0.91 g of powder (subtitled intermediate) with a melting point of 176–179: IR (Nujol) 3206 and 1673 cm$^{-1}$; UV (95% ethanol) 278 nm; NMR (CDCl₃ δ) 7.79–7.91, 7.26–7.37, and 1.45–3.5 the NH and N═CH signals are not visible; mass spectra weak molecular ion at m/e 336 with fragment ions at m/e 216, 201, 172 (base peak) and 91.

Anal. Calcd. for $C_{20}H_{24}N_4O$, mw 336.43: C, 71.40; H, 7.19; N, 16.66. Found: C, 71.06; H, 7.28; N, 16.56.

The mother liquors deposit an additional 2.09 g of crude, wet amidrazone. All of the crude amidrazone is used for the reaction described below.

PART E 1-(Phenylmethyl)-4-(3-phenyl-4H-1,2,4-triazol-4-yl)piperidine.

The crude amidrazone (approximately 12 g, 35.7 mmol) described in Part D of this example is suspended in 80 ml of dry diglyme, then refluxed for 7 hours, cooled overnight, and concentrated in vacuo. The crude material is taken up in $CHCl_3$, extracted with an aqueous 10% NaOH solution, dried over $Na_2SO_4$, and concentrated in vacuo to 9.84 g of tan oil, which is chromatographed over 520 g of silica gel by eluting with 2 liters of 4% methanol/96%$CHCl_3$ and 4 liters of 5% methanol/95% $CHCl_3$, each liter containing 5 ml of concentrated aqueous $NH_4OH$ solution. After a 20 ml forerun, 20 ml fractions are collected. The subtitled product is collected in fractions 51–100 and crystallized as beautiful needles from ethyl acetate/hexane mixtures to afford 4.07 g (35.8% yield from the Formamidine) in two crops with a melting point of 111°–114° C.: IR (Nujol) 1507 cm$^{-1}$; UV (95% ethanol) 228 nm; NMR ($CDCl_3$ δ) 8.34, 4.0, 3.51, 1.99, and 1.82; mass spectra molecular ion at m/e 318 with fragment ions at m/e 317, 289, 241, 227, 173, and 91.

Anal. Calcd. for $C_{20}H_{22}N_4$, nw 318.42: C, 75.43; H, 6.97; N, 17.60. Found: C, 75.14; H, 7.03; N, 17.57.

PART F 4-(3-Phenyl-4H-1,2,4-triazol-4-yl)-piperidine and its dihydrochloride.

The starting benzylamine from Part E above (2.85 g, 8.95 mmol) is dissolved in methanol, treated with ethereal HCl and concentrated in vacuo to a gum, which is taken up in 100 ml of absolute ethanol, treated with 2.8 g of 10% palladium-on-carbon and hydrogenated in a Parr Bomb for 11 days, until no starting material is observed by thin layer chromatography using Silica Gel G, eluting with 10% methanol/90% $CHCl_3$). The catalyst is filtered, and the solvent is removed in vacuo. The product crystallized from methanol/ethyl acetate mixtures to afford 1.19 g (42.2% yield) of prisms with a melting point of 254–260 C: IR (Nujol) 2955 cm$^{-1}$; UV (95% ethanol) 229 nm; NMR ($CDCl_3$, δ) 9.73, 7.77, 3.0–3.7, and 2.5; mass spectra molecular ion peak at m/e 228, with fragment ions at m/e 200, 172, 157, 145, 82, 55, and 36.

Anal. Calcd. for $C_{13}H_{16}N_4$—2HCl—0.5$CH_3OH$, mw 315.22: C, 51.43; H, 6.40; N, 17.78; Cl, 22.49. Found: C, 51.18; H, 6.29; N, 17.53; Cl, 21.19.

Alkylation of this subtitled compound with 2-phenylethyl bromide as described herein produces 1-(2-phenylethyl)-4-(3-phenyl-4H-1,2,4-triazol-4-yl)piperidine, the same compound produced in Example 14, Part B above.

FORMULAS

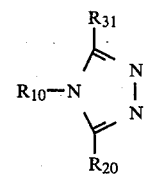

I

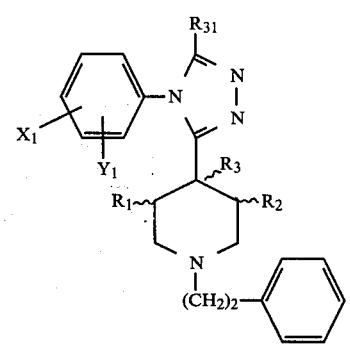

Ia

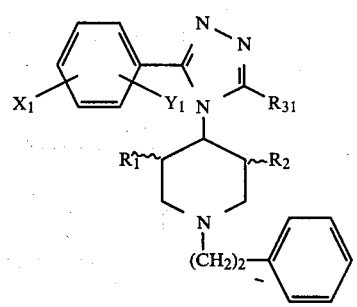

Ib

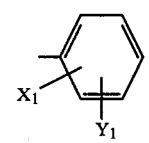

II

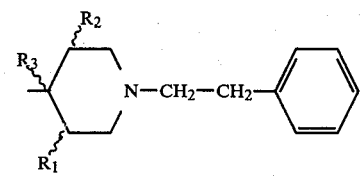

III

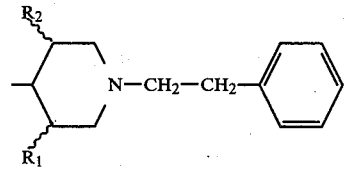

IV

CHART A
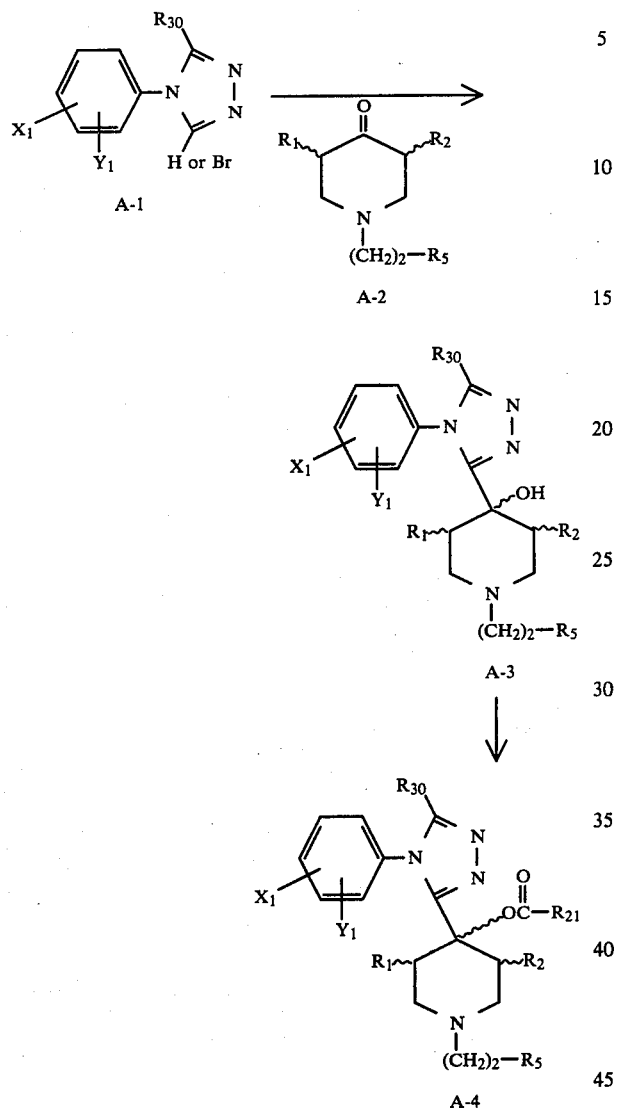
CHART B
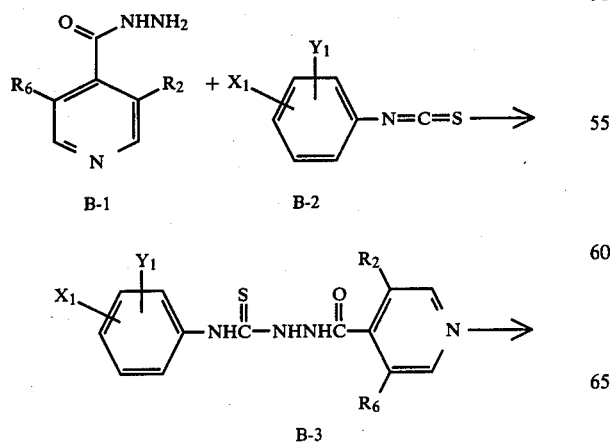
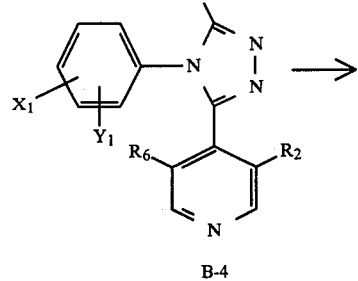
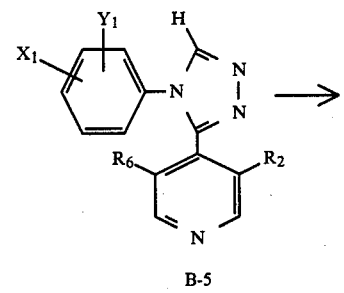
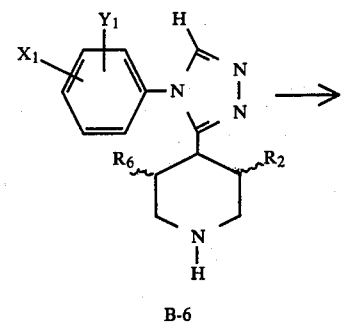
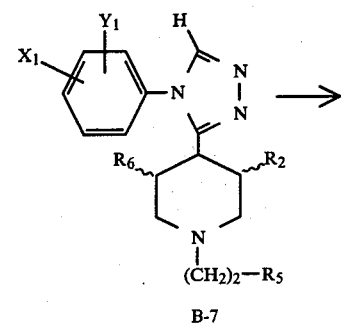

CHART C
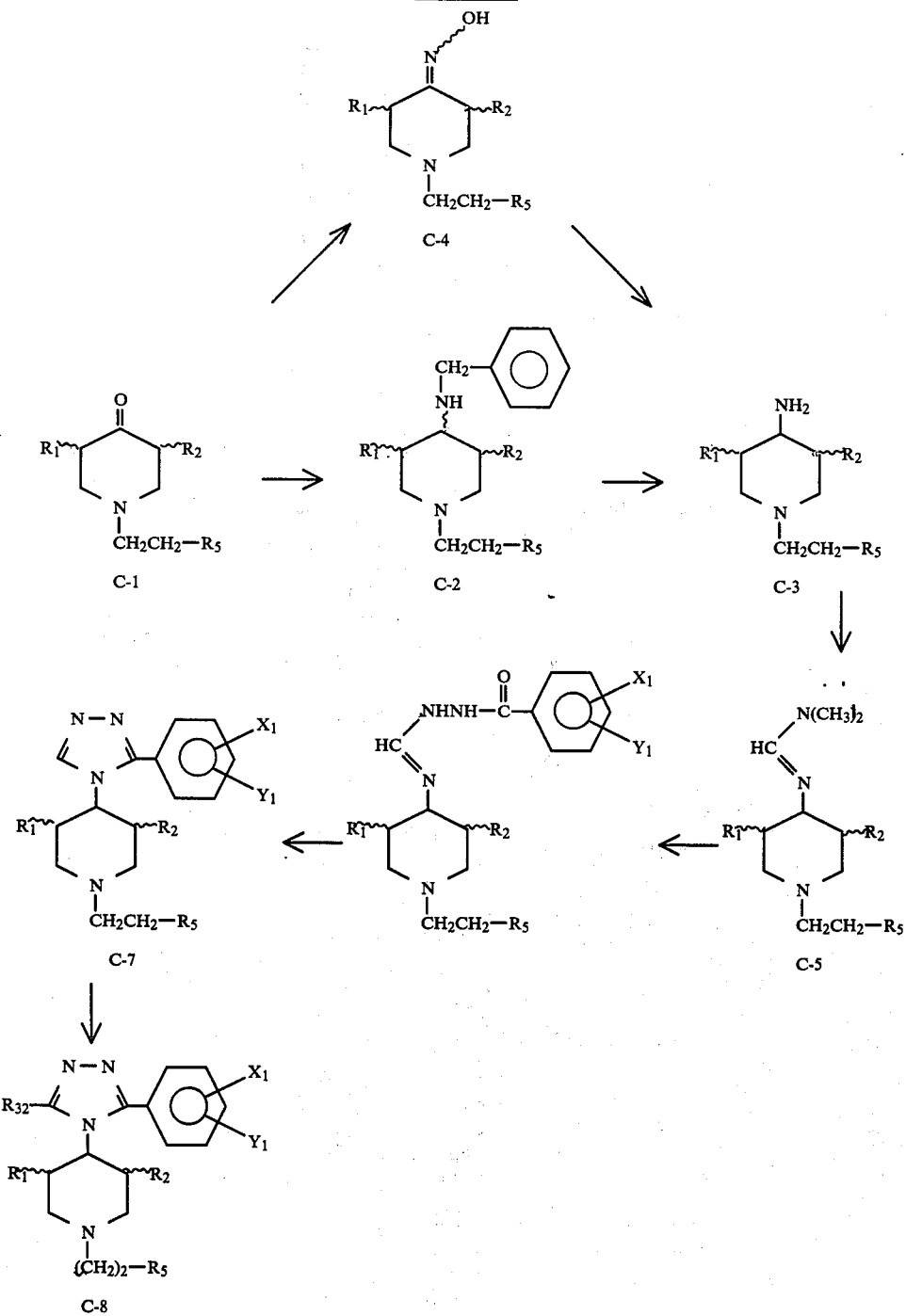
We claim:
1. A compound of the Formula I
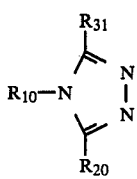
wherein either
(1) $R_{10}$ is a substituent of the Formula II and $R_{20}$ is a substituent of the Formula III or
(2) $R_{10}$ is a substituent of the Formula IV and $R_{20}$ is a substituent of the Formula II;

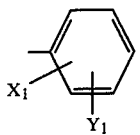

II

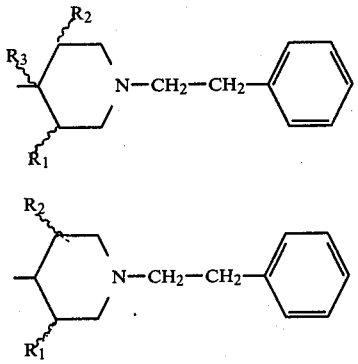

wherein the wavy lines represent the cis or trans configuration;
wherein $R_{31}$ is
(a) hydrogen,
(b) $C_1$ to $C_2$—alkyl,
(c) —$SCH_3$,
(d) —$S(O)CH_3$,
(e) —S—phenyl,
(f) —S(O)—phenyl,
(g) —$CH(OH)CH_3$,
(h) —$CH_2OC(O)R_{11}$, or
(i) phenyl,
with the provisos that
(1) when $R_{20}$ is the Formula III substituent, $R_{31}$ is —$SCH_3$, —$S(O)CH_3$, —S—phenyl, —S(O)—phenyl, —$CH(OH)CH_3$ or —$CH_2OC(O)R_{11}$ only when $R_3$ is hydrogen and
(2) $R_{31}$ is phenyl only when $R_{20}$ is the Formula III substituent and $R_3$ is —$OC(O)R_{21}$;
wherein $X_1$ is
(a) o-, m-, or p-fluoro;
(b) hydrogen,
(c) methoxy,
(d) m-acetoxy, or
(e) ($C_1$-$C_2$)alkyl;
wherein $Y_1$ is
(a) hydrogen,
(b) m-methoxy, or
(c) ($C_1$-$C_2$)alkyl;
with the provisos that $Y_1$ is m-methoxy only when $X_1$ is p-methoxy; and $Y_1$ is ($C_1$-$C_2$)alkyl only when $X_1$ is ($C_1$-$C_2$)alkyl;
wherein $R_1$ is
(a) hydrogen,
(b) —$CH_3$,
(c) —$C_2H_5$, or
(d) $CH_2$=CH—$CH_2$—;
with the proviso that $R_1$ is $CH_2$=CH—$CH_2$— only when $R_{20}$ is a Formula III substituent;
wherein $R_2$ is
(a) hydrogen, or
(b) methyl;
wherein $R_3$ is (a) hydrogen, or
(b) —$OC(O)R_{21}$;
wherein $R_{11}$ and $R_{21}$ are the same or different and are hydrogen, methyl or ethyl; and the pharmacologically acceptable salts thereof.

2. A compound of claim 1 wherein $R_2$ is hydrogen.

3. A compound of claim 2 wherein $R_{31}$ is hydrogen or methyl, $X_1$ is hydrogen, $C_1$ to $C_2$-alkyl in the ortho position, or methoxy, $Y_1$ is hydrogen, m-methoxy, or $C_1$ to $C_2$-alkyl, and $R_1$ is hydrogen or methyl in either stereochemical orientation.

4. A compound of claim 3 wherein $Y_1$ is hydrogen or $C_1$ to $C_2$-alkyl in the ortho position.

5. A compound of claim 2 selected from the group consisting of:
4-[4-(2,6-dimethylphenyl)-5-methyl-4H-1,2,4-triazol-3-yl]-1-(2-phenylethyl)-4-piperidinol, propanoate (ester), and its monohydrobromide;
4-[4-(2,6-dimethylphenyl)-5-methyl-4H-1,2,4-triazol-3-yl]-1-(2-phenylethyl)-4-piperidinol, acetate (ester);
4-(5-ethyl-4-phenyl-4H-1,2,4-triazol-3-yl)-1-(2-phenylethyl)piperidine;
(3α,4α)-4-(5-methyl-4-phenyl-4H-1,2,4-triazol-3-yl)-1-(2-phenylethyl)-3-(2-propenyl)-4-piperidinol, acetate (ester), and its sesquihydrochloride, hemihydrate, slower moving isomer; and
(3α,4β)-4-(5-methyl-4-phenyl-4H-1,2,4-triazol-3-yl)-1-(2-phenylethyl)-3-(2-propenyl)-4-piperidinol, acetate (ester), and its sesquihydrochloride, faster moving isomer.

6. A compound of claim 2 selected from the group consisting of:
4-[4-[3-(acetyloxy)phenyl]-5-methyl-4H-1,2,4-triazol-3-yl]-1-(2-phenylethyl)-4-piperidinol, acetate (ester), and its dihydrochloride, and
4-[4-(2-fluorophenyl)-5-methyl-4H-1,2,4-triazol-3-yl]-1-(2-phenylethyl)-4-piperidinol, acetate ester.

7. A compound of claim 2 selected from the group consisting of:
1-(2-phenylethyl)-4-(4phenyl-4H-1,2,4-triazol-3-yl)-piperidine;
4-(5-methyl-4-phenyl-4H-1,2,4-triazol-3-yl)-1-(2-phenylethyl)-4-piperidinol, acetate (ester);
4-(5-methyl-4-phenyl-4H-1,2,4-triazol-3-yl)-1-(2-phenylethyl)-4-piperidinol, propanoate (ester);
4-(5-methyl-4-phenyl-4H-1,2,4-triazol-3-yl)-1-(2-phenylethyl)-4-piperidinol, formate (ester);
(3α,4β)-3-methyl-4-(5-methyl-4-phenyl-4H-1,2,4-triazol-3-yl)-1-(2-phenylethyl)-4-piperidinol, acetate (ester), and its dihydrochloride, isomer A;
(3α,4β)-3-methyl-4-(5-methyl-4-phenyl-4H-1,2,4-triazol-3-yl)-1-(2-phenylethyl)-4-piperidinol, acetate (ester), and its monohydrochloride, sesquihydrate, isomer B;
4-(5-methyl-4-phenyl-4H-1,2,4-triazol-3-yl)-1-(2-phenylethyl)piperidine;
1-(2-phenylethyl)-4-(3-phenyl-4H-1,2,4-triazol-4-yl)-piperidine;
4-[4-(3-methoxyphenyl)-5-methyl-4H-1,2,4-triazol-3-yl]-1-(2-phenylethyl)-4-piperidinol, acetate (ester); and
4-[4-(2,6-diethylphenyl)-5-methyl-4H-1,2,4-triazol-3-yl]-1-(2-phenylethyl)-4-piperidinol, acetate (ester), and its monohydrochloride, monohydrate.

* * * * *